(12) United States Patent
Dickman et al.

(10) Patent No.: US 8,058,433 B2
(45) Date of Patent: *Nov. 15, 2011

(54) CRYSTALLINE PHARMACEUTICAL

(75) Inventors: Daniel A. Dickman, Longmont, CO (US); Sanjay Chemburkar, Gurnee, IL (US); James J. Fort, Midlothian, VA (US); Rodger F. Henry, Park City, IL (US); David Lechuga-Ballesteros, Santa Clara, CA (US); Yuping Niu, Nyack, NY (US); William Porter, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 1043 days.

This patent is subject to a terminal disclaimer.

(21) Appl. No.: 11/542,075

(22) Filed: Oct. 2, 2006

(65) Prior Publication Data

US 2007/0027172 A1    Feb. 1, 2007

Related U.S. Application Data

(60) Continuation of application No. 10/984,393, filed on Nov. 9, 2004, now abandoned, which is a division of application No. 10/387,175, filed on Mar. 12, 2003, now Pat. No. 6,864,369, which is a division of application No. 09/793,536, filed on Feb. 27, 2001, now Pat. No. 6,608,198.

(60) Provisional application No. 60/193,573, filed on Mar. 30, 2000.

(51) Int. Cl.
*C07D 239/36* (2006.01)
*C07D 239/10* (2006.01)

(52) U.S. Cl. ........................ 544/316; 424/400

(58) Field of Classification Search .................. 544/316; 424/400
See application file for complete search history.

(56) References Cited

U.S. PATENT DOCUMENTS

| | | | |
|---|---|---|---|
| 5,914,332 A | 6/1999 | Sham et al. | |
| 6,232,333 B1 | 5/2001 | Lipari et al. | |
| 6,608,198 B2 | 8/2003 | Dickman et al. | |
| 6,864,369 B2 | 3/2005 | Dickman et al. | |
| 2005/0124810 A1 | 6/2005 | Dickman et al. | |

FOREIGN PATENT DOCUMENTS

| | | |
|---|---|---|
| WO | 96/41813 | 12/1996 |
| WO | WO9641813 A2 | 12/1996 |
| WO | WO9641813 A3 | 12/1996 |
| WO | 98/57648 | 12/1998 |
| WO | WO9857648 A1 | 12/1998 |
| WO | WO0174787 A2 | 10/2001 |
| WO | WO0174787 A3 | 10/2001 |

OTHER PUBLICATIONS

Wilhelm, Michael J. (Journal of Molecular Structure 883-884, pp. 242-248, 2008).*
Hirschmugl, C. J. (Review of Scientific Instruments 66(2, Pt. 2), 1487-8, 1995).*
Freeman, J. E. (Applied Spectroscopy 38(6), 837-43, 1984).*
Duniotz, "Disappearing Polymorphs", Acc. Chem. Res., vol. 28, pp. 193-200 (1995).
Gavezzotti, A., "Are Crystal Structures Predictable?", Acc. Chem. Res., vol. 27, pp. 309-314 (1994).
USP Dictionary of USAN and International Drug Names, p. 509 (lopinavir entry) (2001).
Ö. Almarsson et al., *Novel Approaches to Issues of Developability*, Curr. Drug. Disc. Jan. 6-21, 2003.
J. Bernstein, *Crystal Structure Prediction and Polymorphism*, ACA Transactions 39:14-23 (2004).
J.D. Dunitz et al., *Disappearing Polymorphs*, Acc. Chem. Res. 28(4):193-200 (1995).
J.D. Dunitz, *Are Crystal Structures Predictable*? Chem. Commun: 545-8 (2003).
A. Gavezzotti, *Are Crystal Structures Predictable*? Acc. Chem. Res. 27(10):309-14 (1994).
U.S. Appl. No. 09/538,257, Notice of Abandonment, Jul. 13, 2001.
U.S. Appl. No. 60/177,020, filed Jan. 19, 2000.
U.S. Patent Application Publication No. 2005/0124810, Office Action, Sep. 9, 2005.
U.S. Patent Application Publication No. 2005/0124810, Office Action, Apr. 17, 2006.
U.S. Patent Application Publication No. 2005/0124810, Notice of Abandonment, Nov. 22, 2006.

* cited by examiner

*Primary Examiner* — David Lukton
(74) *Attorney, Agent, or Firm* — Bradley E. Davis

(57) ABSTRACT

New crystalline forms of lopinavir are disclosed.

39 Claims, 31 Drawing Sheets

CRYSTALLINE PHARMACEUTICAL

This application is a continuation of U.S. patent application Ser. No. 10/984,393, filed Nov. 9, 2004, now abandoned, which is a divisional of U.S. patent application Ser. No. 10/387,175, filed Mar. 12, 2003, now U.S. Pat. No. 6,864,369, which is a divisional of U.S. patent application Ser. No. 09/793,536, filed Feb. 27, 2001, now U.S. Pat. No. 6,608,198, which claims the benefit of U.S. Provisional Application No. 60/193,573, filed Mar. 30, 2000. This application incorporates herein by reference the entire contents of U.S. patent application Ser. No. 10/984,393, U.S. patent application Ser. No. 10/387,175, U.S. patent application Ser. No. 09/793,536, and U.S. Provisional Application No. 60/193,573.

TECHNICAL FIELD

This invention relates to novel crystalline forms of (2S,3S,5S)-2-(2,6-dimethylphenoxyacetyl)amino-3-hydroxy-5-(2-(1-tetrahydropyrimid-2-onyl)-3-methylbutanoyl)amino-1,6-diphenylhexane (also known as lopinavir) and methods for their preparation. The novel crystalline forms of the invention can be used to purify or isolate lopinavir or for the preparation of pharmaceutical compositions for the administration of lopinavir.

BACKGROUND OF THE INVENTION

Inhibitors of human immunodeficiency virus (HIV) protease have been approved for use in the treatment of HIV infection for several years. A particularly effective and recently approved HIV protease inhibitor is (2S,3S,5S)-2-(-2,6-dimethylphenoxyacetyl)-amino-3-hydroxy-5-(2-(1-tetrahydropyrimid-2-onyl)-3-methylbutanoyl)amino-1,6-diphenylhexane (also known as lopinavir).

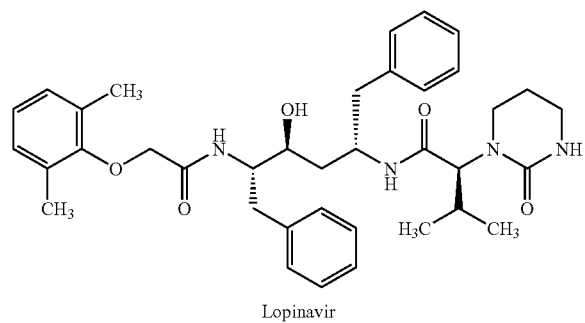

Lopinavir

Lopinavir is known to have utility for the inhibition of HIV protease and the inhibition of HIV infection. Lopinavir is particularly effective for the inhibition of HIV protease and for the inhibition of HIV infection when coadministered with ritonavir. Lopinavir, when combined with ritonavir, is also particularly effective for the inhibition of HIV infection when used in combination with one or more reverse transcriptase inhibitors and/or one or more other HIV protease inhibitors.

Lopinavir and processes for its preparation are disclosed in U.S. Pat. No. 5,914,332, issued Jun. 22, 1999, which is hereby incorporated herein by reference. This patent also discloses processes for preparing amorphous lopinavir.

Pharmaceutical compositions comprising lopinavir or a pharmaceutically acceptable salt thereof are disclosed in U.S. Pat. No. 5,914,332, issued Jun. 22, 1999; U.S. patent application Ser. No. 08/966,495, filed Nov. 7, 1997; U.S. Provisional Application Patent No. 60/177,020, filed Jan. 19, 2000 and U.S. patent application Ser. No. 09/487,739, filed Jan. 19, 2000, all of which are hereby incorporated herein by reference.

It has now been unexpectedly discovered that lopinavir can be prepared and isolated as each of a number of crystal forms.

DISCLOSURE OF THE INVENTION

Figure 1:
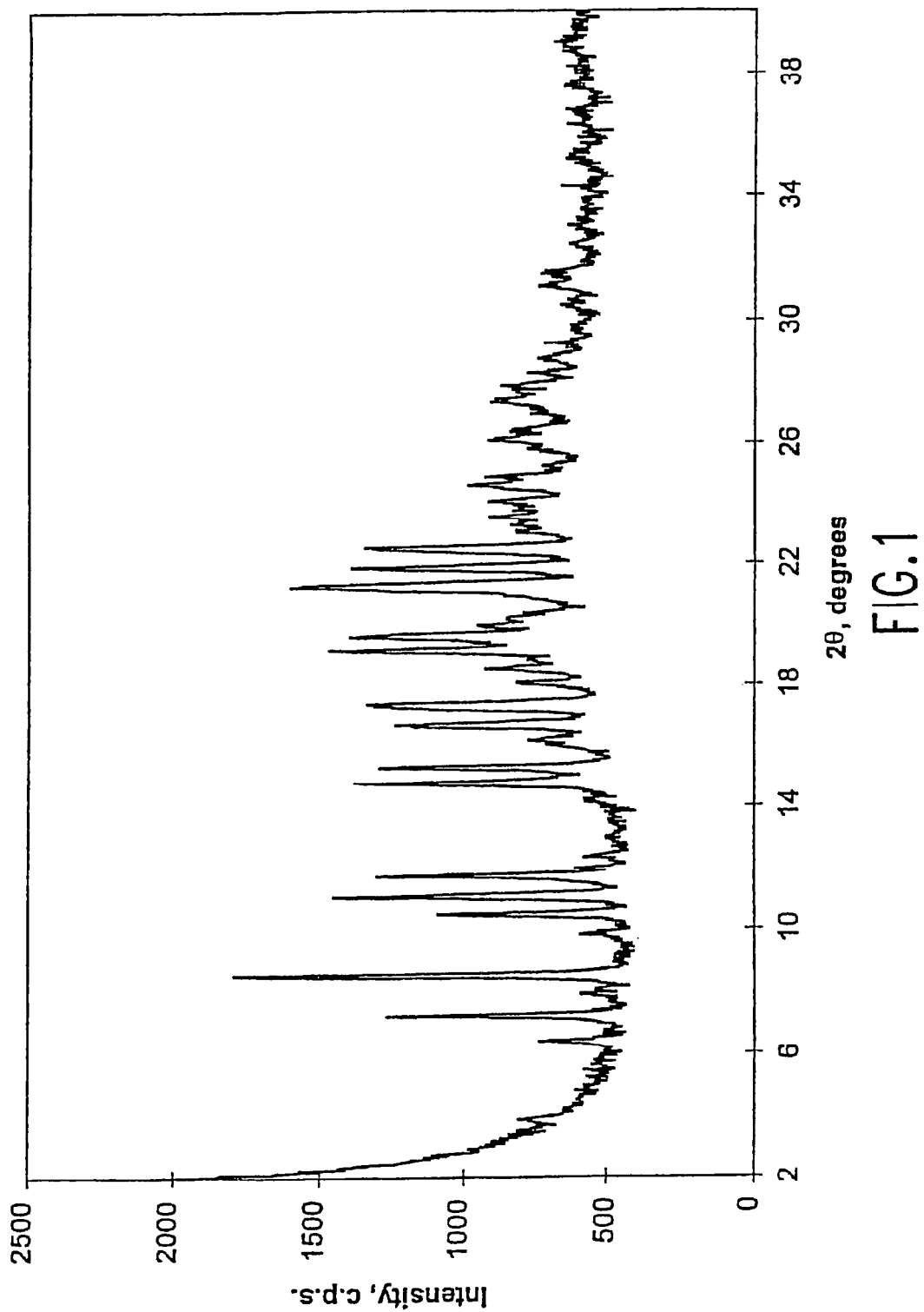
FIG. 1 is the powder X-ray diffraction pattern of the Type I hydrated crystal form of lopinavir comprising about 0.5 molecules of water per molecule of lopinavir.

In accordance with the present invention, there are novel crystal forms of (2S,3S,5S)-2-(2,6-dimethylphenoxyacetyl) amino-3-hydroxy-5-(2-(1-tetrahydropyrimid-2-onyl)-3-methylbutanoyl)amino-1,6-diphenylhexane (lopinavir).

In one embodiment of the present invention there are hydrated crystal forms of lopinavir. For the sake of identification, the hydrated crystal forms are designated as Type I. The Type I hydrated crystal forms of lopinavir comprise from about 0.5 molecules of water per molecule of lopinavir to about 2 molecules of water per molecule of lopinavir.

The Type I hydrated crystal forms of lopinavir are useful in the purification or isolation of lopinavir during the final steps of the process for preparing lopinavir and in the preparation of pharmaceutical compositions for administering lopinavir.

The Type I hydrated crystal form of lopinavir comprising about 0.5 molecules of water per molecule of lopinavir is hygroscopic. Therefore, unless maintained under conditions of about 0% relative humidity, the Type I hydrated crystal form of lopinavir comprises greater than 0.5 molecules of water per molecule of lopinavir. If a Type I hydrated crystal form of lopinavir is dehydrated to below about 0.5 molecules of water per molecule of lopinavir, amorphous lopinavir is obtained.

While the Type I crystal forms of lopinavir comprising 0.5 molecules of water per molecule of lopinavir and about 2 molecules of water per molecule of lopinavir represent the lower and upper ranges, respectively, of water of salvation observed for crystalline Type I hydrated forms of lopinavir, water content of the crystal form may vary within this range depending on the temperature and water content of the environment of the crystal form. The term "Type I higher hydrated crystal form" will be used herein to refer to the Type I hydrated crystal forms of lopinavir comprising from greater than 0.5 molecules of water per molecule of lopinavir up to about 2 molecules of water per molecule of lopinavir. Preferably, the Type I higher hydrated crystal form of lopinavir comprises from about 0.75 to about 1.9 molecules of water per molecule of lopinavir. More preferably, the Type I higher hydrated crystal form of lopinavir comprises from about 1.0 to about 1.8 molecules of water per molecule of lopinavir.

In a preferred embodiment, the Type I hydrated crystal forms of lopinavir are substantially pure, relative to other forms of lopinavir, including amorphous, solvated forms, non-solvated and desolvated forms.

It has been found that the solid state FT mid-infrared spectrum is a means of characterizing the Type I hydrated crystal forms of lopinavir and differentiating the hydrated crystal forms from other crystal forms of lopinavir.

The Type I hydrated crystal forms of lopinavir (including the substantially pure Type I hydrated crystal forms of lopinavir) have the characteristic solid state FT mid-infrared bands shown in Table 1. Table 1 shows the range of peak positions for each of 17 characteristic mid-infrared bands in the solid state FT mid-IR spectrum of Type I hydrated crystal forms of lopinavir. This means that any Type I hydrated crystal form of lopinavir will have a peak at a position within the range (minimum to maximum) for each of peaks shown in Table 1.

Most characteristic of the Type I hydrated crystal forms of lopinavir (including the substantially pure Type I hydrated crystal forms of lopinavir) are the positions of the solid state FT mid-infrared bands for the amide bond carbonyl stretching. These bands are located within the ranges 1652-1666 cm$^{-1}$ and 1606-1615 cm$^{-1}$ for the Type I hydrated crystal forms of lopinavir. Any Type I hydrated crystal form of lopinavir (including the substantially pure Type I hydrated crystal forms of lopinavir) will have a peak at a position within the range 1652-1666 cm$^{-1}$ and a peak at a position within the range 1606-1615 cm$^{-1}$.

The Type I hydrated crystal forms of lopinavir (including the substantially pure Type I hydrated crystal forms of lopinavir) are further characterized by a solid state infrared peak at a position within each of the ranges 778-783 cm$^{-1}$, 765-769 cm$^{-1}$, 755-759 cm$^{-1}$ and 738-742 cm$^{-1}$.

TABLE 1

Ranges of Peak Positions for Solid State FT Mid-IR Bands for Type I Hydrated Crystal Forms of Lopinavir

| Minimum cm$^{-1}$ | Maximum cm$^{-1}$ | Intensity* |
| --- | --- | --- |
| 3495 | 3505 | W/absent |
| 3371 | 3386 | S/MS |
| 3281 | 3299 | MS |
| 3058 | 3064 | W |
| 3024 | 3031 | W |
| 2958 | 2967 | M |
| 2926 | 2938 | W |
| 2868 | 2875 | W |
| 1652 | 1666 | VS |
| 1606 | 1615 | S/MS |
| 1524 | 1532 | S |
| 1450 | 1456 | MS |
| 1404 | 1410 | W/VW |
| 1304 | 1311 | MS |
| 1187 | 1197 | MS |
| 1089 | 1094 | M |
| 1048 | 1056 | W |

*W = weak; M = moderate; MS = moderately strong; S = strong; VS = very strong

The Type I crystal form of lopinavir comprising about 0.5 molecules of water per molecule of lopinavir has the powder X-ray diffraction pattern which appears in FIG. 1. The Type I crystal form of lopinavir comprising about 0.5 molecules of water per molecule of lopinavir has the solid state $^{13}$C nuclear magnetic resonance spectrum, FT near infrared spectrum and FT mid infrared spectrum which appear in FIGS. 2, 3 and 4, respectively. The sample from which the infrared and nuclear magnetic resonance spectra were obtained may contain somewhat more than 0.5 molecules of water per molecule of lopinavir due to the hygroscopicity of the crystal form when the level of hydration is about 0.5 molecules of water per molecule of lopinavir.

The two-theta angle positions of characteristic peaks in the powder X-ray diffraction pattern of the Type I hydrated crystal form of lopinavir comprising about 0.5 molecules of water per molecule of lopinavir (including the substantially pure Type I hydrated crystal forms of lopinavir comprising about 0.5 molecules of water per molecule of lopinavir) as shown in FIG. 1 are: 7.25°±0.1°, 8.53°±0.1°, 10.46°±0.1°, 11.05°±0.1°, 11.71°±0.1°, 14.76°±0.1°, 15.30°±0.1°, 16.67°±0.1°, 17.32°±0.1°, 19.10°±0.1°, 19.57°±0.1°, 21.24°±0.1°, 21.84°±0.1° and 22.46°±0.1°.

The Type I hydrated crystal form of lopinavir comprising about 0.5 molecules of water per molecule of lopinavir can be prepared from the Type I hydrated crystal form of lopinavir comprising greater than 0.5 molecules of water per molecule of lopinavir by dehydrating at 0% relative humidity. If dehydration continues beyond the stage of the hemihydrate, amorphous lopinavir is obtained.

The Type I hydrated crystal form of lopinavir can be prepared from solution or suspension in water or from solutions in mixtures of water and water miscible organic solvents. Examples of water miscible organic solvents include C1-C4 alcohols such as methanol, ethanol and the like; acetonitrile; and the like. In the mixtures of water and water miscible organic solvents, the amount of water can vary from about 10% by volume to about 90% by volume (preferably, from about 40% to about 60% by volume). In a preferred method, the Type I higher hydrated crystal form of lopinavir can be prepared by crystallization of hydrated lopinavir from a warm solution in a mixture of water and ethanol, followed by extended exposure to an elevated relative humidity environment.

In addition, the Type I higher hydrated crystal form of lopinavir can be prepared by hydrating the Type I hemihydrate crystal form of lopinavir at elevated relative humidity (for example, at relative humidity of about 20% or more).

The Type I higher hydrated crystal form of lopinavir has the powder X-ray diffraction pattern, solid state $^{13}C$ nuclear magnetic resonance spectrum, solid state FT near infrared spectrum and solid state FT mid infrared spectrum which appear in FIGS. 5, 6, 7 and 8, respectively.

Figure 5:
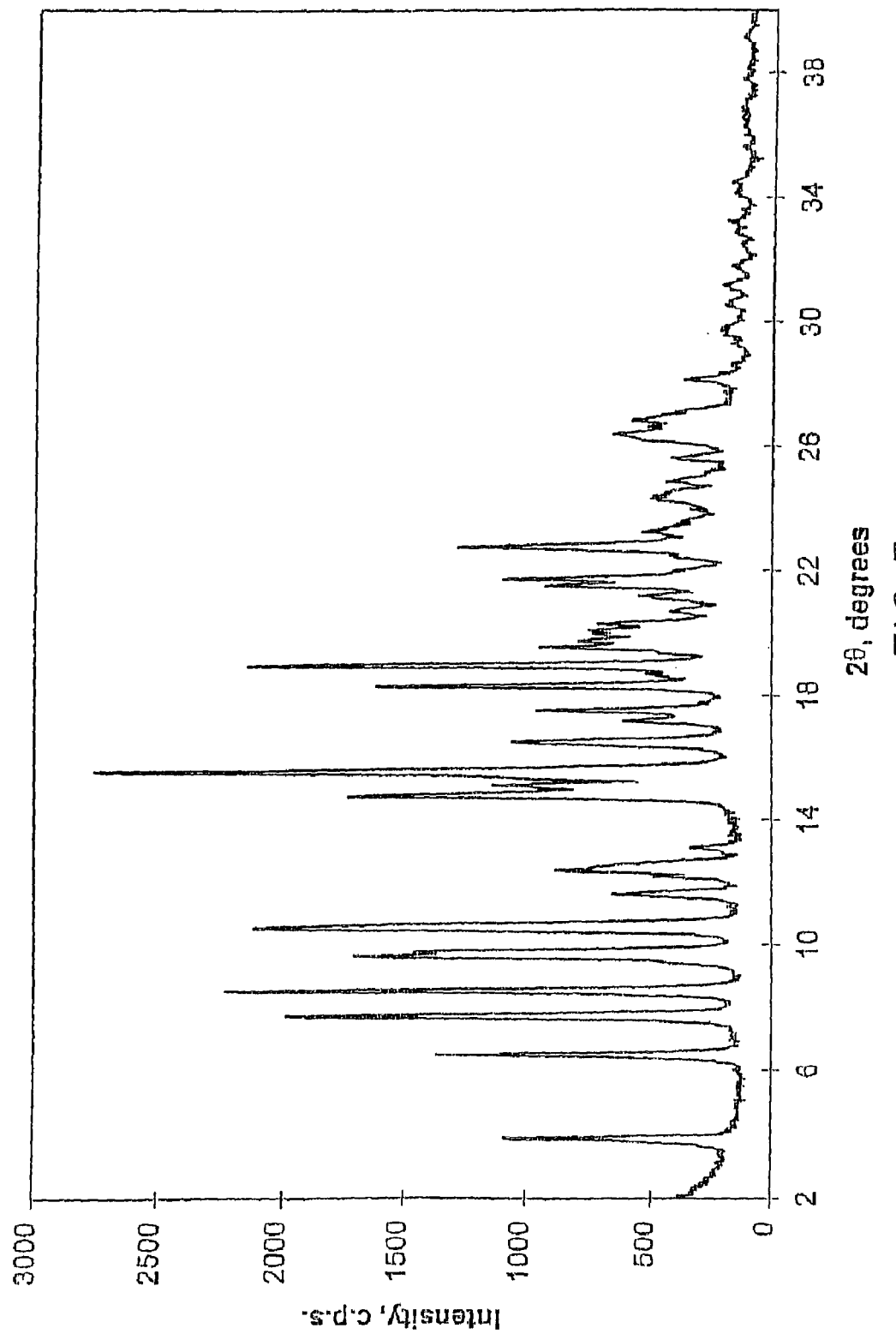
FIG. 5 is the powder X-ray diffraction pattern of a Type I higher hydrated crystal form of lopinavir.

The two-theta angle positions of characteristic peaks in the powder X-ray diffraction pattern of the Type I higher hydrated crystal form of lopinavir (including the substantially pure Type I higher hydrated crystal form of lopinavir) as shown in FIG. 5 are: 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°.

More preferably, the Type I higher hydrated crystal form of lopinavir (including the substantially pure Type I higher hydrated crystal form of lopinavir) is characterized by peaks in the powder X-ray diffraction pattern having two-theta angle positions as shown in FIG. 5 of: 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

The single crystal X-ray parameters and experimental details for the Type I higher hydrated crystal form of lopinavir are as follows.

Single Crystal X-Ray Parameters and Experimental Details for the Type I Higher Hydrated Crystal Form of Lopinavir

| Experimental Details | |
|---|---|
| Crystal Data | |
| Crystal System | Monoclinic |
| Lattice Parameters | a = 46.922 (2) Å |
| | b = 13.9945 (4) Å |
| | c = 11.7231 (4) Å |
| | β = 105.605 (1)° |
| | V = 7414.2 (4) Å$^3$ |
| Space Group | c2 (#5) |
| Z Value | 8 |
| $D_{calc}$ | 1.19 g/cm$^3$ |
| Intensity Measurements | |
| Diffractometer | Bruker SMART |
| Radiation | Mo Kα (λ = 0.7107 Å) |
| Temperature | ambient |
| $2θ_{max}$ | 46.6° |
| Correction | Lorentz-polarization |
| Number of Reflections Measured | Total: 27795 |
| Structure Solution and Refinement | |
| Number of Observations (I > 3.0 σ(I)) | 5368 |
| Number of Variables | 932 |
| Reflections/Parameter Ratio | 5.76 |
| Residuals: R; $R_w$ | 0.107; 0.128 |

In two further embodiments of the present invention there are solvated crystal forms of lopinavir. Based on single crystal X-ray structure determination, the first embodiment of the solvated crystal forms of lopinavir involves a crystal structure in which stacks of lopinavir molecules are held together by hydrogen bond interactions and aligned along the short crystallographic axis. The solvent molecules play no role in the hydrogen bonding, but simply fill pockets that exist between the stacks of lopinavir molecules. For the sake of identification, the solvated crystal forms of lopinavir of this embodiment are designated as Type II.

Based on single crystal X-ray structure determination, the second embodiment of the solvated crystal forms of lopinavir involves a crystal structure in which the molecules of lopinavir are hydrogen bonded in sheets. The sheets of hydrogen bonded lopinavir molecules are wrinkled, producing channels that are occupied by varying amounts of solvent molecules. The solvent molecules play no role in the hydrogen bonding of the second embodiment of solvated crystal forms of lopinavir. For the sake of identification, the solvated crystal forms of lopinavir of this embodiment are designated as Type III.

Type II

The Type II solvated crystal forms of lopinavir are useful for the purification or isolation of lopinavir during the final steps of the process for preparing lopinavir.

The Type II solvated crystal forms of lopinavir are particularly useful for obtaining crystalline lopinavir which is free from, or has greatly reduced amounts of, a variety of the impurities that result during the process for preparing lopinavir.

The Type II solvated crystal forms of lopinavir are typically hemisolvates. In other words, for every asymmetric unit of the crystal there are two molecules of lopinavir and one molecule of solvent. Lower levels of solvation are also possible. The Type II solvated crystal forms of lopinavir can be partially desolvated by drying under vacuum with heating. However, if more than about 75% of the maximum allowable solvent (maximum allowable is hemisolvated) is removed, amorphous lopinavir is obtained. Therefore, the Type II solvated crystal forms of lopinavir comprise from about 0.125 molecules of solvent per molecule of lopinavir to about 0.5 molecules of solvent per molecule of lopinavir.

The Type II solvated crystal forms of lopinavir comprise relatively small polar organic solvents. Examples of such relatively small polar organic solvents include methanol, ethanol, n-propanol, isopropanol, n-butanol, iso-butanol, t-butanol, n-amyl alcohol, iso-amyl alcohol, t-pentanol, ethyl acetate, acetone, tetrahydrofuran, chloroform, methylene chloride, propylene glycol, methylethyl ketone, dimethylsulfoxide and the like.

In a preferred embodiment, the Type II solvated crystal forms of lopinavir are substantially pure, relative to other forms of lopinavir, including amorphous, hydrated forms, other solvated forms, non-solvated and desolvated forms.

It has been found that the solid state FT mid-infrared spectrum is a means for characterizing the Type II solvated crystal forms of lopinavir and differentiating the Type II solvated crystal forms of lopinavir from other crystal forms of lopinavir.

The Type II solvated crystal forms of lopinavir (including the substantially pure Type II solvated crystal forms of lopinavir) have the characteristic solid state FT mid-infrared bands shown in Table 2. Table 2 shows the range of peak positions for each of the 18 characteristic mid-infrared bands in the solid state FT mid-IR spectrum of Type II solvated crystal forms of lopinavir. This means that any Type II solvated crystal form of lopinavir will have a peak at a position within the range (minimum to maximum) for each of the peaks shown in Table 2.

Most characteristic of the Type II solvated crystal forms of lopinavir (including the substantially pure Type II solvated crystal forms of lopinavir) are the positions of the solid state FT mid-infrared bands for the amide bond carbonyl stretching. These bands are located within the ranges 1661-1673 $cm^{-1}$, 1645-1653 $cm^{-1}$ and 1619-1629 $cm^{-1}$ for the Type II solvated crystal forms of lopinavir. Any Type II solvated crystal form of lopinavir (including the substantially pure Type II solvated crystal forms of lopinavir) will have a peak at a position within the range 1661-1673 $cm^{-1}$, a peak at a position within the range 1645-1653 $cm^{-1}$ and a peak at a position within the range 1619-1629 $cm^{-1}$.

The Type II solvated crystal forms of lopinavir (including the substantially pure Type II solvated crystal forms of lopinavir) are further characterized by a solid state infrared peak at a position within each of the ranges 776-781 $cm^{-1}$, 767-771 $cm^{-1}$, 747-758 $cm^{-1}$ and 742-746 $cm^{-1}$.

TABLE 2

Ranges of Peak Positions for Solid State FT Mid-IR Bands for Type II Solvated Crystal Forms of Lopinavir

| Minimum $cm^{-1}$ | Maximum $cm^{-1}$ | Intensity* |
|---|---|---|
| 3391 | 3415 | M |
| 3324 | 3340 | MS |
| 3057 | 3063 | W |
| 3023 | 3029 | W |
| 2961 | 2970 | M |

TABLE 2-continued

Ranges of Peak Positions for Solid State FT Mid-IR Bands for Type II Solvated Crystal Forms of Lopinavir

| Minimum $cm^{-1}$ | Maximum $cm^{-1}$ | Intensity* |
|---|---|---|
| 2913 | 2938 | W |
| 2866 | 2879 | W |
| 1661 | 1673 | S |
| 1645 | 1653 | S |
| 1619 | 1629 | VS |
| 1540 | 1548 | MS |
| 1514 | 1522 | S |
| 1450 | 1456 | MS |
| 1418 | 1426 | M |
| 1302 | 1309 | M |
| 1181 | 1193 | MS |
| 1089 | 1095 | M |
| 1045 | 1056 | W |

*W = weak; M = moderate; MS = moderately strong; S = strong; VS = very strong

The solid state FT mid-infrared spectra of Type II solvated crystal forms of lopinavir (isopropanol, ethyl acetate and chloroform) appear in FIGS. 9, 10, 11, 12 and 13. The solid state FT near infrared spectra of Type II solvated crystal forms of lopinavir (isopropanol, ethyl acetate and chloroform) appear in FIGS. 14, 15, 16, 17 and 18.

The Type II solvated crystal forms of lopinavir can be prepared by suspending excess solid lopinavir in the solvent and allowing the suspension to equilibrate over time. The Type II solvated crystal form of lopinavir is then isolated by filtration.

The Type II solvated crystal forms of lopinavir can also be prepared by cooling a supersaturated solution of lopinavir in the solvent, with or without the addition of seed crystals. The Type II solvated crystal form of lopinavir is then isolated by filtration.

The Type II solvated crystal forms of lopinavir can also be prepared by allowing slow evaporation of the solvent from a solution of lopinavir. The Type II solvated crystal form of lopinavir is then isolated by filtration.

The Type II solvated crystal forms of lopinavir can also be prepared by slowly adding an antisolvent to a heated solution of lopinavir in the solvent, thereby inducing crystallization. The Type II solvated crystal form of lopinavir is then isolated by filtration.

The single crystal X-ray parameters and experimental details for the Type II ethyl acetate hemisolvate crystal form of lopinavir and the Type II chloroform hemisolvate crystal form of lopinavir are as follows.

Single Crystal X-Ray Parameters and Experimental Details for the Type II Ethyl Acetate Hemisolvate Crystal Form of Lopinavir

| Experimental Details | |
|---|---|
| Crystal Data | |
| Crystal System | Monoclinic |
| Lattice Parameters | a = 11.3456 (1) Å |
| | b = 33.9490 (2) Å |
| | c = 9.8641 (2) Å |
| | β = 89.930 (1)° |
| | V = 3799.37 (7) Å$^3$ |
| Space Group | P2$_1$ (#4) |

-continued

Experimental Details

| | |
|---|---|
| Z Value | 4 |
| $D_{calc}$ | 1.18 g/cm$^3$ |
| Intensity Measurements | |
| Diffractometer | Bruker SMART |
| Radiation | Mo Kα (λ = 0.7107 Å) |
| Temperature | ambient |
| $2\theta_{max}$ | 46.7° |
| Correction | Lorentz-polarization |
| Number of Reflections Measured | Total: 14824 |
| | Unique: 5211 |
| Structure Solution and Refinement | |
| Number of Observations (I > 3.0 σ(I)) | 4411 |
| Number of Variables | 882 |
| Reflections/Parameter Ratio | 5.0 |
| Residuals: R; R$_w$ | 0.104; 0.099 |

Single Crystal X-Ray Parameters and Experimental Details for the Type II Chloroform Hemisolvate Crystal Form of Lopinavir Experimental Details

| | |
|---|---|
| Crystal Data | |
| Crystal System | Orthorhombic |
| Lattice Parameters | a = 9.7703 (51) Å |
| | b = 33.410 (2) Å |
| | c = 11.4874 (6) Å |
| | V = 3749.8 (3) Å$^3$ |
| Space Group | P2$_1$2$_1$2 (#18) |
| Z Value | 4 |
| $D_{calc}$ | 1.22 g/cm$^3$ |
| Intensity Measurements | |
| Diffractometer | Bruker SMART |
| Radiation | Mo Kα (λ = 0.7107 Å) |
| Temperature | ambient |
| $2\theta_{max}$ | 46.6° |
| Correction | Lorentz-polarization |
| Number of Reflections Measured | Total: 14960 |
| | Unique: 4359 |
| Structure Solution and Refinement | |
| Number of Observations (I > 3.0 σ(I)) | 4234 |
| Number of Variables | 438 |
| Reflections/Parameter Ratio | 9.67 |
| Residuals: R; R$_w$ | 0.094; 0.104 |

Type III

The Type III solvated crystal forms of lopinavir are useful in the purification or isolation of lopinavir during the final steps of the process for preparing lopinavir.

The Type III solvated crystal forms of lopinavir are particularly useful for obtaining crystalline lopinavir which is free from, or has greatly reduced amounts of, a variety of the impurities that result during the process for preparing lopinavir.

The Type III solvated crystal forms of lopinavir are the thermodynamically stable crystal forms isolated from solvents that generally comprise hydrophobic organic solvents or solvents too large to fit within the crystal lattice of the Type II solvated crystal forms of lopinavir. The Type III solvated crystal forms of lopinavir comprise solvents including n-hexanol, n-octanol, 3-ethyl-3-pentanol, polyethylene glycol, ethyl acetate, isopropyl acetate, n-butyl acetate, glycerol triacetate, acetone, methyl isobutyl ketone, 2,4-dimethylpentanone, alpha-tetralone, methyl t-butyl ether, 2,2,4,4-tetramethyltetrahydrofuran, isosorbide dimethyl ether, toluene, tetralin, nitrobenzene, p-xylene, sulfolane, hexane, heptane, decalin, oleic acid and the like.

In a preferred embodiment, the Type III solvated crystal forms of lopinavir are substantially pure, relative to other forms of lopinavir, including amorphous, hydrated forms, other solvated forms, non-solvated and desolvated forms.

It has been found that the solid state FT mid-infrared spectrum is a means for characterizing the Type III solvated forms of lopinavir and differentiating the Type III solvated crystal forms of lopinavir from other crystal forms of lopinavir.

The Type III solvated crystal forms of lopinavir (including the substantially pure Type III solvated crystal forms of lopinavir) have the characteristic solid state FT mid-infrared bands shown in Table 3. Table 3 shows the range of peak positions for each of the 16 characteristic mid-infrared bands in the solid state FT mid-IR spectrum of Type III solvated crystal forms of lopinavir. This means that any Type III solvated crystal form of lopinavir will have a peak at a position within the range (minimum to maximum) for each of the peaks shown in Table 3.

Most characteristic of the Type III solvated crystal forms of lopinavir (including the substantially pure Type III solvated crystal forms of lopinavir) are the positions of the solid state FT mid-infrared bands for the amide bond carbonyl stretching. A band is located within the range 1655-1662 cm$^{-1}$ for the Type III solvated crystal forms of lopinavir. Frequently, a second band is located within the range 1636-1647 cm$^{-1}$ for the Type III solvated crystal forms of lopinavir. However, in some instances the second band (in the range 1636-1647 cm$^{-1}$) appears as a shoulder on the first band or is not well enough resolved from the first band to be distinguishable as a second band. Any Type III solvated crystal form of lopinavir (including the substantially pure Type III solvated crystal forms of lopinavir) will have a peak at a position within the range 1655-1662 cm$^{-1}$ and may also have a peak at a position within the range 1636-1647 cm$^{-1}$.

The Type III solvated crystal forms of lopinavir (including the substantially pure Type III solvated crystal forms of lopinavir) are further characterized by a solid state infrared peak at a position within each of the ranges 772-776 cm$^{-1}$, 766-770 cm$^{-1}$ and 743-747 cm$^{-1}$.

Figure 31:
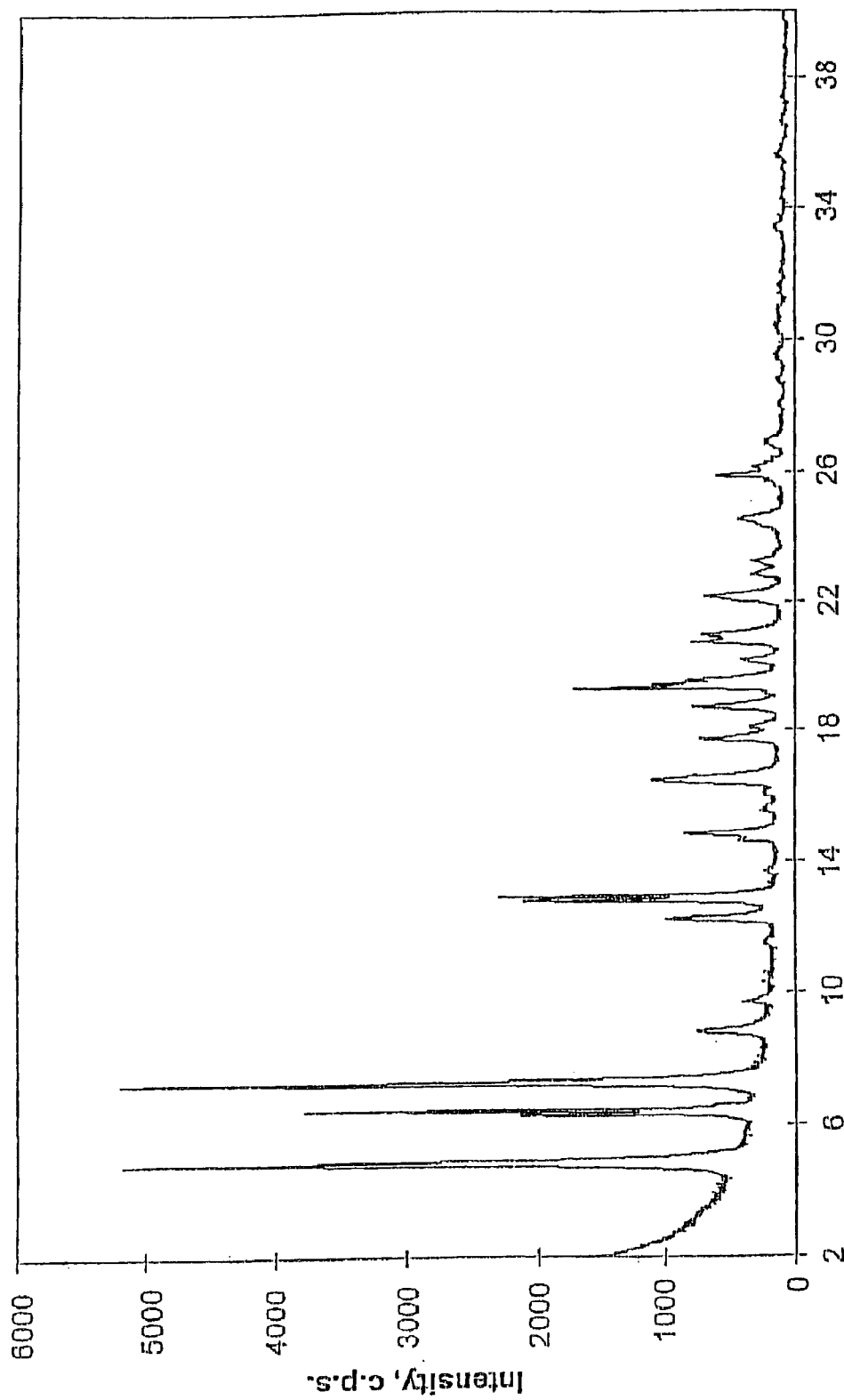
FIG. 31 is the powder X-ray diffraction pattern of the Type III solvated (ethyl acetate) crystal form of lopinavir.

The two-theta angle positions of characteristic peaks in the powder X-ray diffraction pattern of the Type III solvated (ethyl acetate) crystal form of lopinavir (including the substantially pure Type III solvated (ethyl acetate) crystal form of lopinavir) as shown in FIG. 31 are: 4.85°±0.1°, 6.52°±0.1°, 7.32°0.1°, 12.82°±0.1°, 12.96°±0.1°, 16.49°±0.1° and 19.31°–0.1°.

TABLE 3

Ranges of Peak Positions for Solid State FT Mid-IR Bands for Type III Solvated and Desolvated Crystal Forms of Lopinavir

| Minimum cm$^{-1}$ | Maximum cm$^{-1}$ | Intensity* |
|---|---|---|
| 3394 | 3405 | S |
| 3278 | 3302 | MS |
| 3061 | 3071 | W |
| 3024 | 3033 | W |
| 2954 | 2965 | M |
| 2924 | 2939 | W |
| 2853 | 2872 | W |
| 1655 | 1662 | VS |
| 1636 | 1647 | S |

TABLE 3-continued

Ranges of Peak Positions for Solid State FT Mid-IR Bands for Type III Solvated and Desolvated Crystal Forms of Lopinavir

| Minimum cm$^{-1}$ | Maximum cm$^{-1}$ | Intensity* |
|---|---|---|
| 1517 | 1525 | S |
| 1501 | 1513 | MS |
| 1450 | 1455 | MS |
| 1300 | 1309 | MS |
| 1193 | 1200 | MS |
| 1090 | 1098 | W |
| 1051 | 1057 | M |

*W = weak; M = moderate; MS = moderately strong; S = strong; VS = very strong

Figure 19:
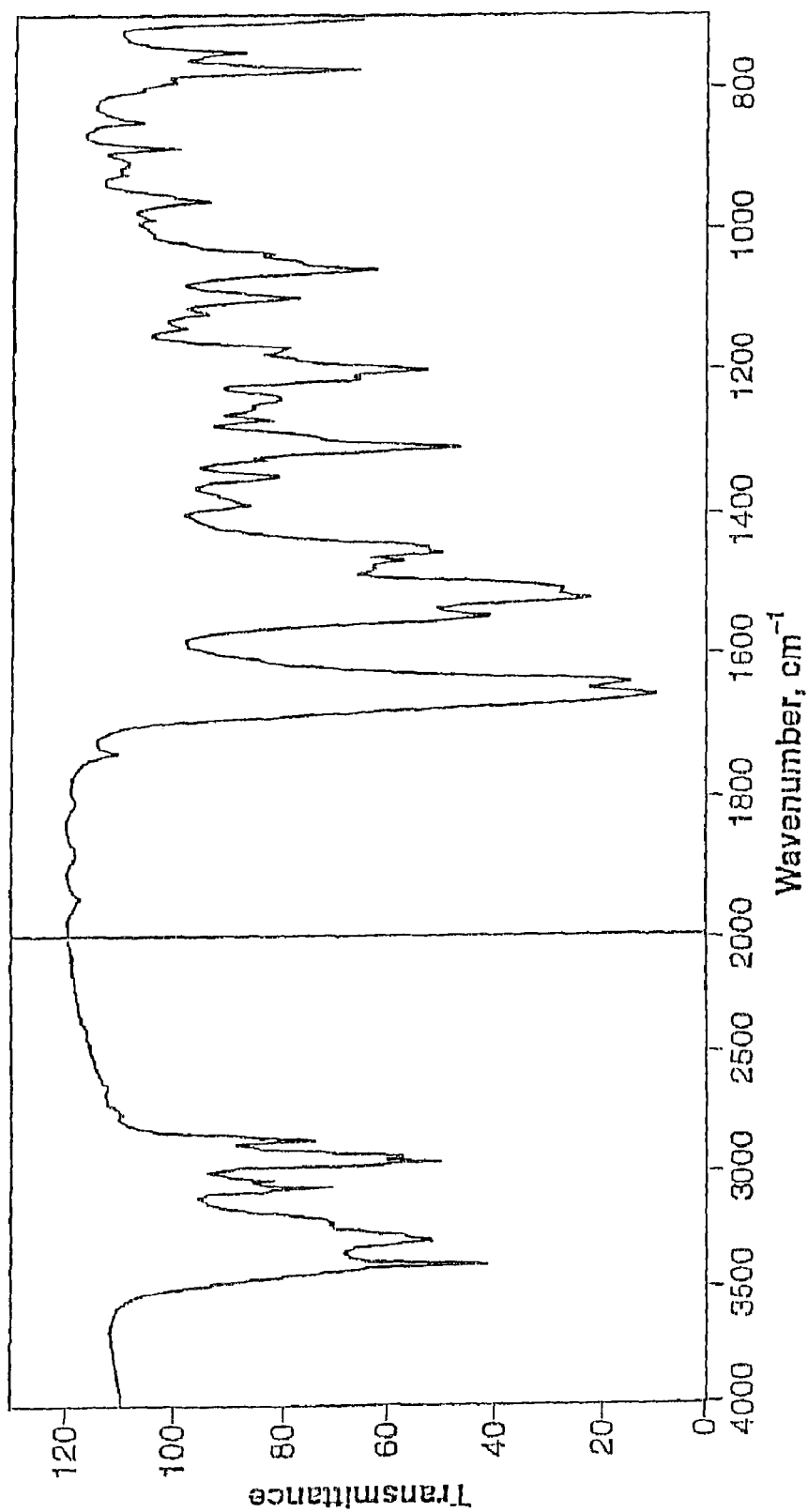
FIG. 19 is the solid state FT mid-infrared spectrum of the Type III ethyl acetate solvated crystal form of lopinavir.

The solid state FT mid-infrared spectrum of the Type III ethyl acetate solvated crystal form of lopinavir appears in FIG. 19. The solid state FT near infrared spectrum of the Type III ethyl acetate solvated crystal form of lopinavir appears in FIG. 20.

The Type III solvated crystal forms of lopinavir can be prepared by suspending excess solid lopinavir in the solvent and allowing the suspension to equilibrate over time. The Type III solvated crystal form of lopinavir is then isolated by filtration.

The Type III solvated crystal forms of lopinavir can also be prepared by cooling a supersaturated solution of lopinavir in the solvent, with or without the addition of seed crystals. The Type III solvated crystal form of lopinavir is then isolated by filtration.

The Type III solvated crystal forms of lopinavir can also be prepared by allowing slow evaporation of the solvent from a solution of lopinavir. The Type III solvated crystal form of lopinavir is then isolated by filtration.

The Type III solvated crystal forms of lopinavir can also be prepared by slowly adding an antisolvent to a heated solution of lopinavir in the solvent, thereby inducing crystallization. The Type III solvated crystal form of lopinavir is then isolated by filtration.

Single Crystal X-Ray Parameters and Experimental Details for the Type III Ethyl Acetate Solvated Crystal Form of Lopinavir

| Experimental Details | |
|---|---|
| Crystal Data | |
| Crystal System | Orthorhombic |
| Lattice Parameters | a = 23.961 (9) Å |
| | b = 27.58 (1) Å |
| | c = 11.967 (4) Å |
| | V = 7907 (5) Å$^3$ |
| Space Group | C222$_1$ (#20) |
| Z Value | 8 |
| Intensity Measurements | |
| Diffractometer | Rigaku AFC5R |
| Radiation | Cu Kα (λ = 1.54178 Å) |
| Temperature | ambient |
| 2θ$_{max}$ | 120.2° |
| Correction | Lorentz-polarization |
| | Absorption |
| | (trans. Factors: 0.87-1.00) |
| Number of Reflections Measured | Total: 6520 |
| | Unique: 6520 |
| Structure Solution and Refinement | |
| Number of Observations (I > 3.0 σ(I)) | 2154 |
| Number of Variables | 443 |
| Reflections/Parameter Ratio | 4.86 |
| Residuals: R; R$_w$ | 0.096; 0.093 |

One example of a Type III desolvated crystal form of lopinavir has been prepared from acetonitrile. From all other solvents it has not been possible to prepare a fully desolvated Type III crystal form of lopinavir.

The Type III desolvated crystal form of lopinavir is useful in the purification or isolation of lopinavir and in the preparation of pharmaceutical compositions for administering lopinavir.

It has been found that the solid state FT mid-infrared spectrum is a means for characterizing the Type III desolvated form of lopinavir and differentiating the Type III desolvated crystal forms of lopinavir from other crystal forms of lopinavir, except the Type III solvated crystal form.

The Type III desolvated crystal form of lopinavir (including the substantially pure Type III desolvated crystal form of lopinavir) also has the characteristic solid state FT mid-infrared bands shown in Table 3. Table 3 shows the range of peak positions for each of the 16 characteristic mid-infrared bands in the solid state FT mid-IR spectrum of Type III desolvated crystal form of lopinavir. This means that the Type III desolvated crystal form of lopinavir will have a peak at a position within the range (minimum to maximum) for each of the peaks shown in Table 3.

Most characteristic of the Type III desolvated crystal form of lopinavir (including the substantially pure Type III desolvated crystal form of lopinavir) are the positions of the solid state FT mid-infrared bands for the amide bond carbonyl stretching. A band is located within the range 1655-1662 cm$^{-1}$ for the Type III desolvated crystal form of lopinavir. Frequently, a second band (in the range 1636-1647 cm$^{-1}$) appears as a shoulder on the first band or is not well enough resolved from the first band to be distinguishable as a second band. Any Type III desolvated crystal form of lopinavir (including the substantially pure Type III desolvated crystal form of lopinavir) will have a peak at a position within the range 1655-1662 cm$^{-1}$ and may also have a peak at a position within the range 1636-1647 cm$^{-1}$ as a shoulder on the peak at a position within the range 1655-1662 cm$^{-1}$.

Figure 21:
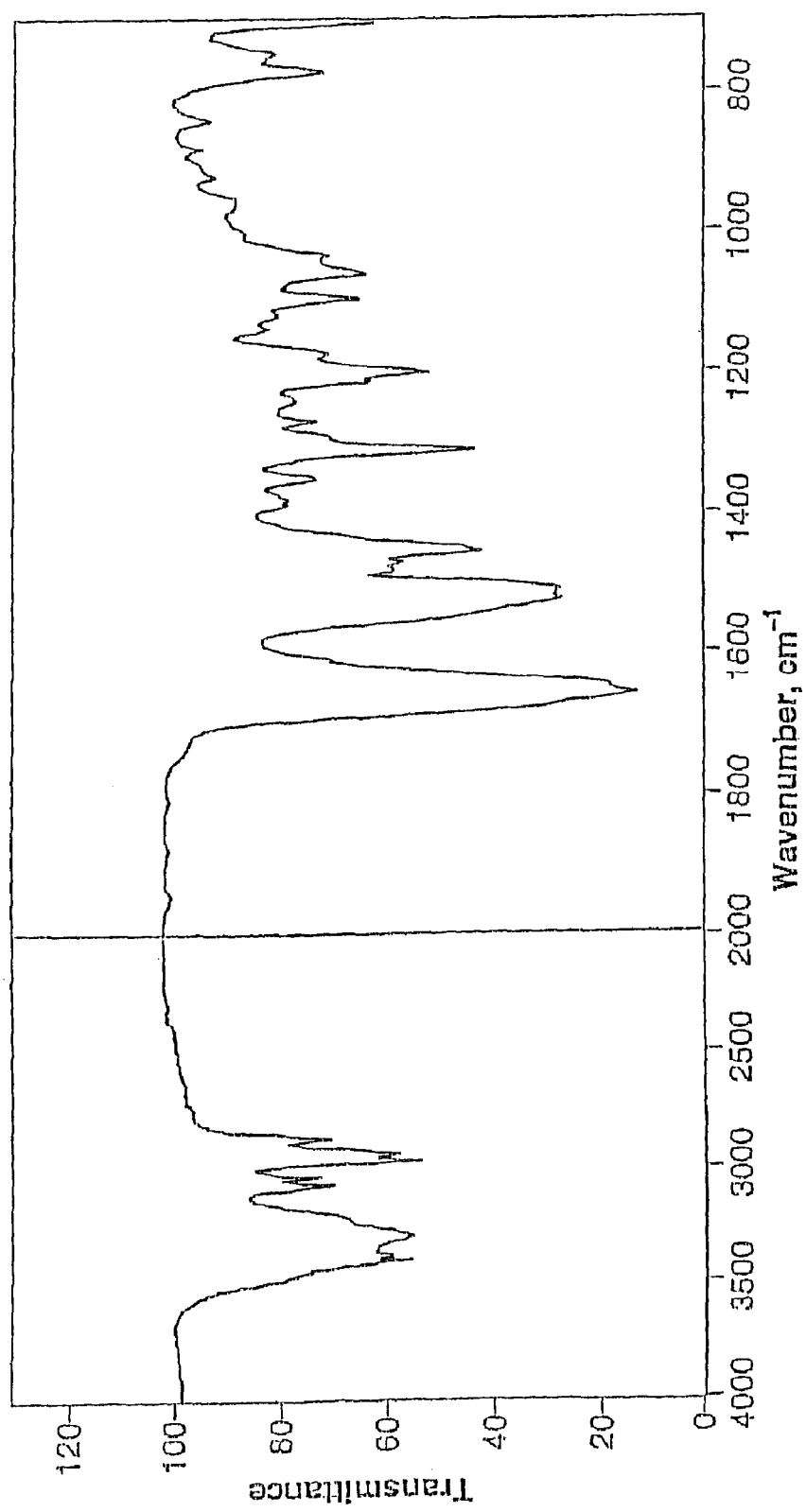
FIG. 21 is the solid state FT mid-infrared spectrum of the Type III desolvated crystal form of lopinavir.

The solid state FT mid-infrared spectrum of the Type III desolvated crystal form of lopinavir appears in FIG. 21. The solid state FT near infrared spectrum of the Type III desolvated crystal form of lopinavir appears in FIG. 22. The powder X-ray diffraction pattern of the Type III desolvated crystal form of lopinavir appears in FIG. 23. The 100 MHz solid state $^{13}$C nuclear magnetic resonance spectrum of the Type III desolvated crystal form of lopinavir appears in FIG. 24. The DSC thermogram of the Type III desolvated crystal form of lopinavir appears in FIG. 25.

The DSC thermogram of the Type III desolvated crystal form of lopinavir exhibits a melting endotherm with onset at 95° C. and peak at 98° C. (ΔH=18 J/g) when differential scanning calorimetry is performed with a scanning rate of 1° C./minute to 150° C. for a sample which lost 0.0% of its initial weight upon heating at 1° C./minute to 150° C.

Figure 23:
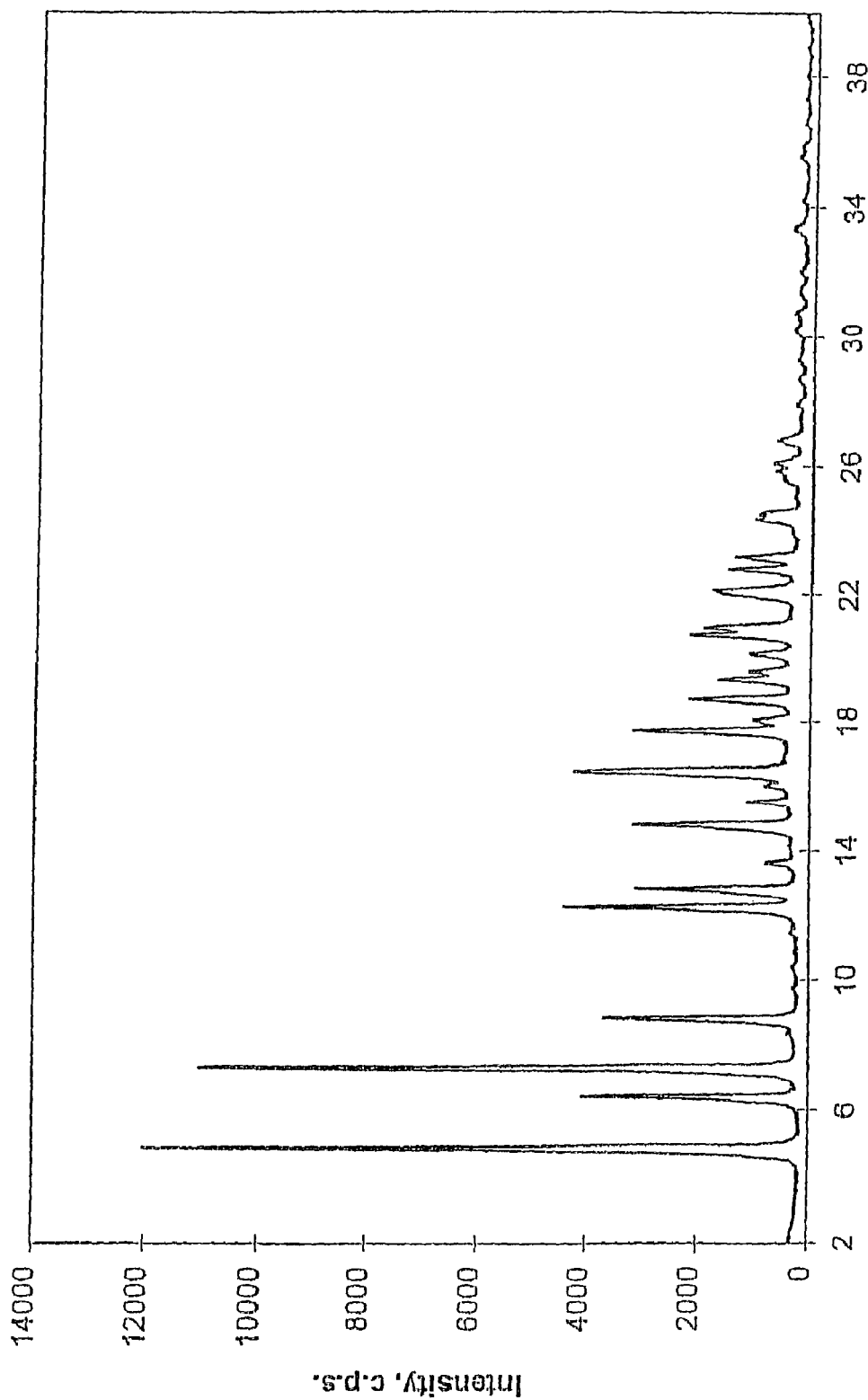
FIG. 23 is the powder X-ray diffraction pattern of the Type III desolvated crystal form of lopinavir.

The two-theta angle positions of characteristic peaks in the powder X-ray diffraction pattern of the Type III desolvated crystal form of lopinavir (including the substantially pure Type III desolvated crystal form of lopinavir) as shown in FIG. 23 are: 4.85°±0.1°, 6.39°±0.1°, 7.32°±0.1°, 8.81°±0.1°, 12.20°±0.1°, 12.81°±0.1°, 14.77°±0.1°, 16.45°±0.1° and 17.70°±0.1°.

More preferably, the Type III desolvated crystal form of lopinavir (including the substantially pure Type III desolvated crystal form of lopinavir) is characterized by peaks in the powder X-ray diffraction pattern having two-theta angle positions as shown in FIG. 23 of: 4.85°±0.1°, 6.39°±0.1°, 7.32°±0.1°, 8.81°±0.1°, 12.20°±0.1°, 12.81°±0.1°, 14.77°±0.1°, 16.45°±0.1°, 17.70°±0.1°, 18.70°±0.1°, 20.68°±0.1°, 20.92°±0.1°, 22.06°±0.1° and 22.76°±0.1°.

Single Crystal X-Ray Parameters and Experimental Details for the Type III Desolvated Crystal Form of Lopinavir

| Experimental Details | |
|---|---|
| Crystal Data | |
| Crystal System | Orthorhombic |
| Lattice Parameters | a = 24.0465 (10) Å |
| | b = 27.5018 (11) Å |
| | c = 11.9744 (3) Å |
| | V = 7918.9 (8) Å$^3$ |
| Space Group | C222$_1$ (#20) |
| Z Value | 8 |
| D$_{calc}$ | 1.055 g/cm$^3$ |
| Intensity Measurements | |
| Diffractometer | Nonius KappaCCD |
| Radiation | Mo Kα (λ = 0.71073 Å) |
| Temperature | ambient |
| 2θ$_{max}$ | 61° |
| Number of Reflections Measured | Total: 28494 |
| | Unique: 5148 |
| Structure Solution and Refinement | |
| Number of Observations (I > 2.0 σ(I)) | 4069 |
| Number of Variables | 442 |
| Reflections/Parameter Ratio | 9.21 |
| Residuals: R; R$_w$ | 0.056; 0.116 |

In yet another embodiment of the present invention there is a non-solvated crystal form of lopinavir. For the sake of identification, the non-solvated crystal form of lopinavir of this embodiment is designated as Type IV.

The Type IV non-solvated crystal form of lopinavir is useful in the purification or isolation of lopinavir and in the preparation of pharmaceutical compositions for administering lopinavir.

In a preferred embodiment, the Type IV non-solvated crystal forms of lopinavir are substantially pure, relative to other forms of lopinavir, including amorphous, hydrated forms, solvated forms, other non-solvated and desolvated forms.

It has been found that the solid state FT mid-infrared spectrum is a means of characterizing the Type IV non-solvated crystal form of lopinavir and differentiating the Type IV non-solvated crystal form from other crystal forms of lopinavir.

The Type IV non-solvated crystal form of lopinavir (including the substantially pure Type IV non-solvated crystal forms of lopinavir) has the characteristic solid state FT mid-infrared bands shown in Table 4. Table 4 shows the range of peak positions for each of 19 characteristic mid-infrared bands in the solid state FT mid-IR spectrum of Type IV non-solvated crystal form of lopinavir. This means that any Type IV non-solvated crystal form of lopinavir will have a peak at a position within the range (minimum to maximum) for each of peaks shown in Table 4. When the solid state mid-IR spectrum is obtained at a resolution of 4 cm$^{-1}$, a peak at a position in one or more of the following additional characteristic bands may also be observed: 1668-1674 cm$^{-1}$ (strong), 1656-1662 cm$^{-1}$ (strong), 1642-1648 cm$^{-1}$ (strong). At higher resolution, or after Fourier deconvolution, these additional peaks are distinguishable.

Most characteristic of the Type IV non-solvated crystal form of lopinavir (including the substantially pure Type IV non-solvated crystal forms of lopinavir) is the positions of the solid state FT mid-infrared bands for the amide bond carbonyl stretching. These bands are located within the ranges 1680-1685 cm$^{-1}$ and 1625-1630 cm$^{-1}$ for the Type IV non-solvated crystal form of lopinavir. In addition, especially at higher resolution, bands are located within the ranges 1668-1674 cm$^{-1}$, 1656-1662 cm$^{-1}$ and 1642-1648 cm$^{-1}$. Any Type IV non-solvated crystal form of lopinavir (including the substantially pure Type IV non-solvated crystal forms of lopinavir) will have a peak at a position within the range 1680-1685 cm$^{-1}$ and a peak at a position within the range 1625-1630 cm$^{-1}$ and may also have a peak at a position within the range 1668-1674 cm$^{-1}$, a peak within the range 1656-1662 cm$^{-1}$ and a peak within the range 1642-1648 cm$^{-1}$.

The Type IV non-solvated crystal form of lopinavir (including the substantially pure Type IV non-solvated crystal form of lopinavir) is further characterized by a solid state infrared peak at a position within each of the ranges 780-784 cm$^{-1}$, 764-768 cm$^{-1}$ and 745-749 cm$^{-1}$.

TABLE 4

Ranges of Peak Positions for Solid State FT Mid-IR Bands for Type IV Non-Solvated Crystal Form of Lopinavir

| Minimum cm$^{-1}$ | Maximum cm$^{-1}$ | Intensity* |
|---|---|---|
| 3433 | 3439 | M |
| 3415 | 3421 | M |
| 3406 | 3412 | M |
| 3338 | 3345 | MS |
| 3309 | 3315 | M |
| 3272 | 3278 | M |
| 3082 | 3089 | W |
| 3025 | 3030 | W |
| 2959 | 2965 | M |
| 2926 | 2932 | W |
| 2870 | 2875 | W |
| 1680 | 1685 | S |
| 1625 | 1630 | VS |
| 1514 | 1526 | S |
| 1451 | 1456 | MS |
| 1306 | 1312 | M |
| 1189 | 1194 | M |
| 1089 | 1094 | W |
| 1044 | 1050 | W |

*W = weak; M = moderate; MS = moderately strong; S = strong; VS = very strong

The Type IV non-solvated crystal form of lopinavir has the solid state FT mid infrared spectrum, the solid state FT near infrared spectrum, the powder X-ray diffraction pattern, solid state $^{13}$C nuclear magnetic resonance spectrum and differential scanning calorimetric (DSC) thermogram which appear in FIGS. 26, 27, 28, 29 and 30, respectively.

Figure 28:
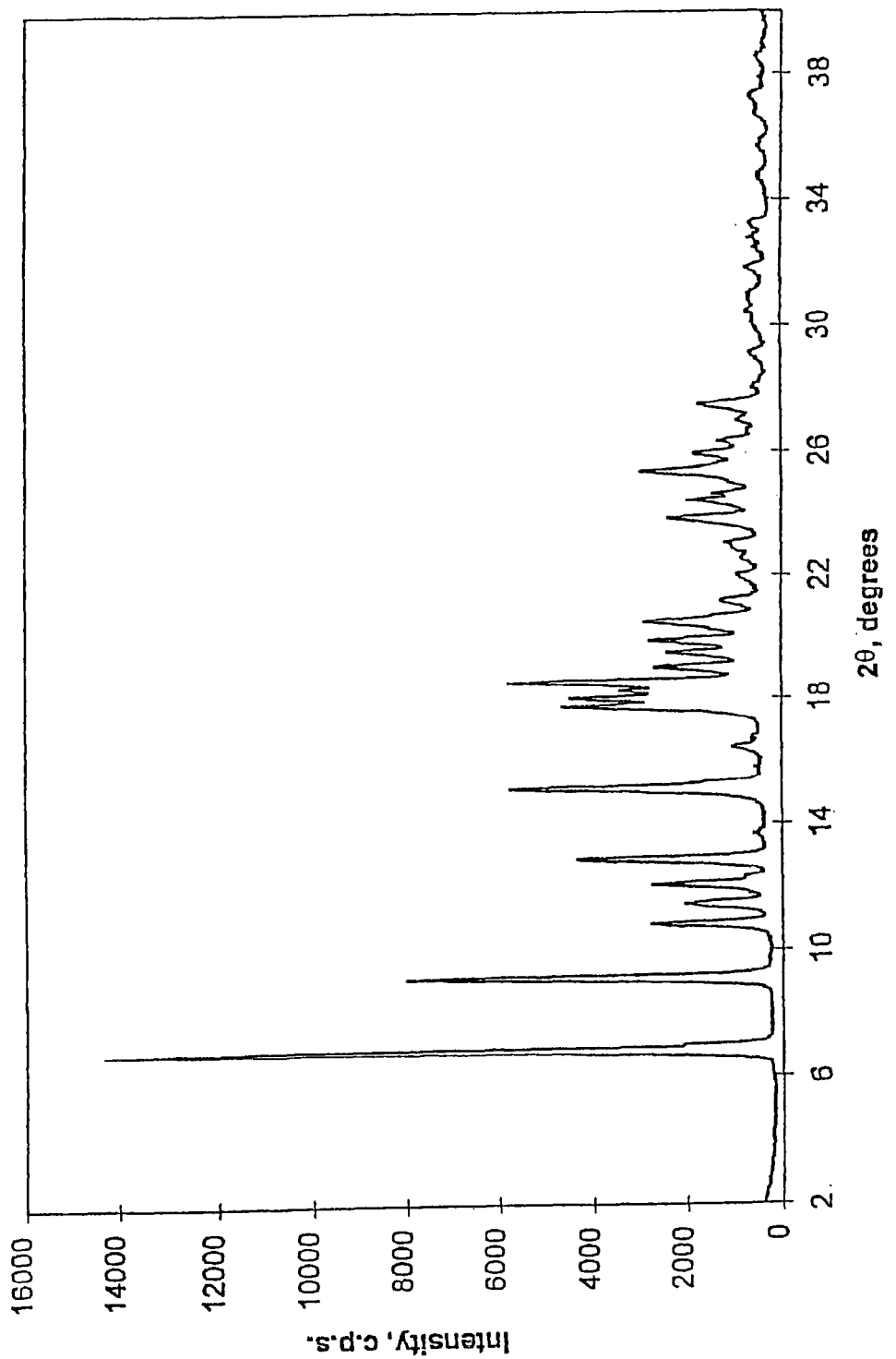
FIG. 28 is the powder X-ray diffraction pattern of the Type IV non-solvated crystal form of lopinavir.

The two-theta angle positions of characteristic peaks in the powder X-ray diffraction pattern of the Type IV non-solvated crystal form of lopinavir (including the substantially pure Type IV non-solvated crystal forms of lopinavir) as shown in FIG. 28 are: 6.85°±0.1°, 9.14°±0.1°, 12.88°±0.1°, 15.09°±0.1°, 17.74°±0.1°, 18.01°±0.1° and 18.53°±0.1°.

More preferably, the Type IV non-solvated crystal form of lopinavir (including the substantially pure Type IV non-solvated crystal forms of lopinavir) is characterized by peaks in the powder X-ray diffraction pattern having two-theta angle positions as shown in FIG. 28 of: 6.85°±0.1°, 9.14°±0.1°, 10.80°±0.1°, 12.04°±0.1°, 12.88°±0.1°, 15.09°±0.1°, 17.74°±0.1°, 18.01°±0.1°, 18.26°±0.1°, 18.53°±0.1°, 20.47°±0.1° and 25.35°±0.1°.

The DSC thermogram of the Type IV non-solvated crystal form of lopinavir exhibits a melting endotherm with onset at 117° C. and peak at 122° C. (ΔH=47 J/g) when differential scanning calorimetry is performed with a scanning rate of 1° C./minute to 150° C.

The single crystal X-ray parameters and experimental details for the Type IV non-solvated crystal form of lopinavir are as follows.

Single Crystal X-Ray Parameters and Experimental Details for the Type IV Non-Solvated Crystal Form of Lopinavir

| Experimental Details | |
|---|---|
| Crystal Data | |
| Crystal System | Orthorhombic |
| Lattice Parameters | a = 15.065 (8) Å |
| | b = 25.27 (1) Å |
| | c = 9.732 (3) Å |
| | V = 3704 (3) Å$^3$ |
| Space Group | P2$_1$2$_1$2$_1$ (#20) |
| Z Value | 4 |
| D$_{calc}$ | 1.13 g/cm$^3$ |
| Intensity Measurements | |
| Diffractometer | Rigaku AFC5R |
| Radiation | Cu Kα (λ = 1.54178 Å) |
| Temperature | ambient |
| 2θ$_{max}$ | 120.2° |
| Correction | Lorentz-polarization |
| | Absorption |
| | (trans. Factors: 0.8362-0.9496 |
| Number of Reflections Measured | Total: 3145 |
| Structure Solution and Refinement | |
| Number of Observations (I > 3.0 σ(I)) | 1434 |
| Number of Variables | 415 |
| Reflections/Parameter Ratio | 3.46 |
| Residuals: R; R$_w$ | 0.081; 0.085 |

The Type IV non-solvated crystal form of lopinavir can be prepared from acetonitrile by slow cooling and slow evaporation of a saturated solution or by exposure of amorphous lopinavir to an acetonitrile atmosphere. In addition, a solution of lopinavir in acetonitrile can be seeded with Type IV non-solvated lopinavir crystals to produce more Type IV non-solvated crystal form of lopinavir.

The following examples will serve to further illustrate the preparation of the novel crystalline forms of lopinavir of the invention.

Example 1

Preparation of a Type I Higher Hydrated Crystal Form of Lopinavir

A saturated solution of lopinavir was prepared at room temperature in a mixture of 20 mL of ethanol and 40 mL of water. The saturated solution was stirred at room temperature and water (54 mL) was slowly added at a rate of 0.15 mL/minute using a syringe pump. After stirring overnight, the resulting precipitate (crystals) was suction filtered.

Example 2

Preparation of a Type I Higher Hydrated Crystal Form of Lopinavir

An NMR tube was filled with 1.75 mL of water. Then 0.5 mL of a solution of lopinavir in ethanol (99.482 mg of lopinavir/mL ethanol) was very carefully layered on top of the water. The tube capped to prevent evaporation and was allowed to stand undisturbed. Crystals of the Type I hydrated crystal form of lopinavir comprising greater than 0.5 molecules of water per molecule of lopinavir were obtained after about 30 days.

Example 3

Preparation of a Type I Higher Hydrated Crystal Form of Lopinavir

Figure 6:
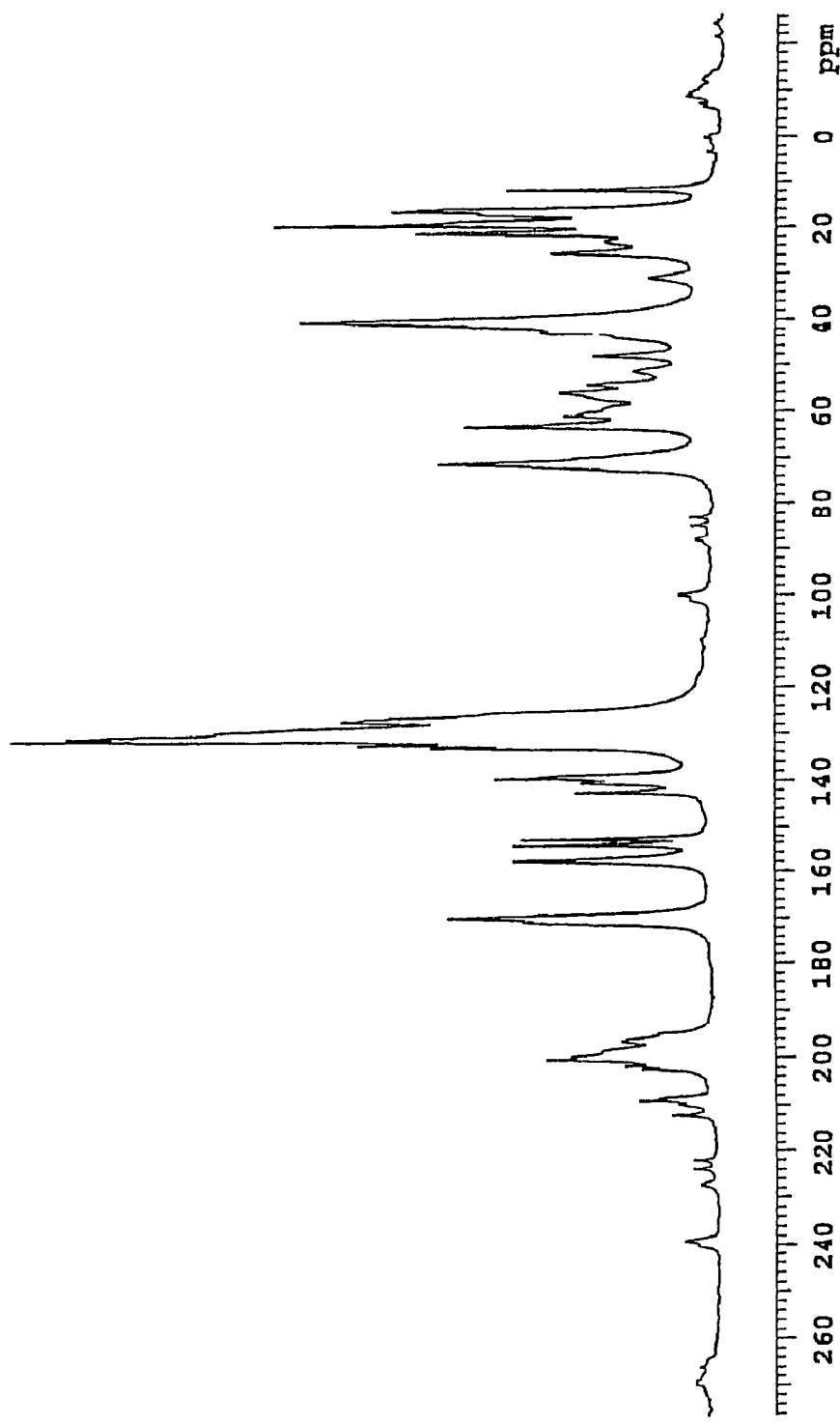
FIG. 6 is the 100 MHz solid state $^{13}C$ nuclear magnetic resonance spectrum of a Type I higher hydrated crystal form of lopinavir.
Figure 7:
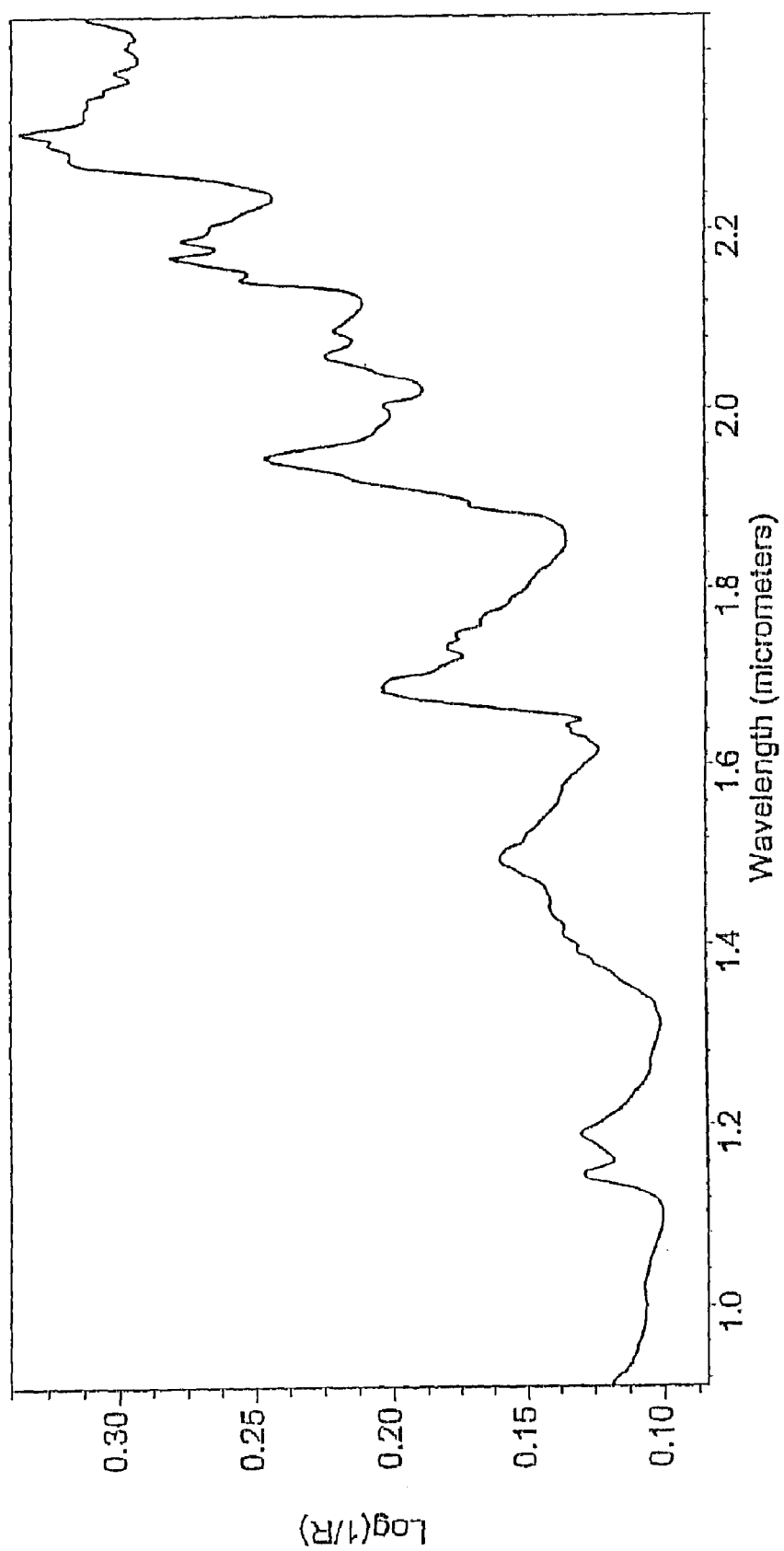
FIG. 7 is the solid state FT near infrared spectrum of a Type I higher hydrated crystal form of lopinavir.
Figure 8:
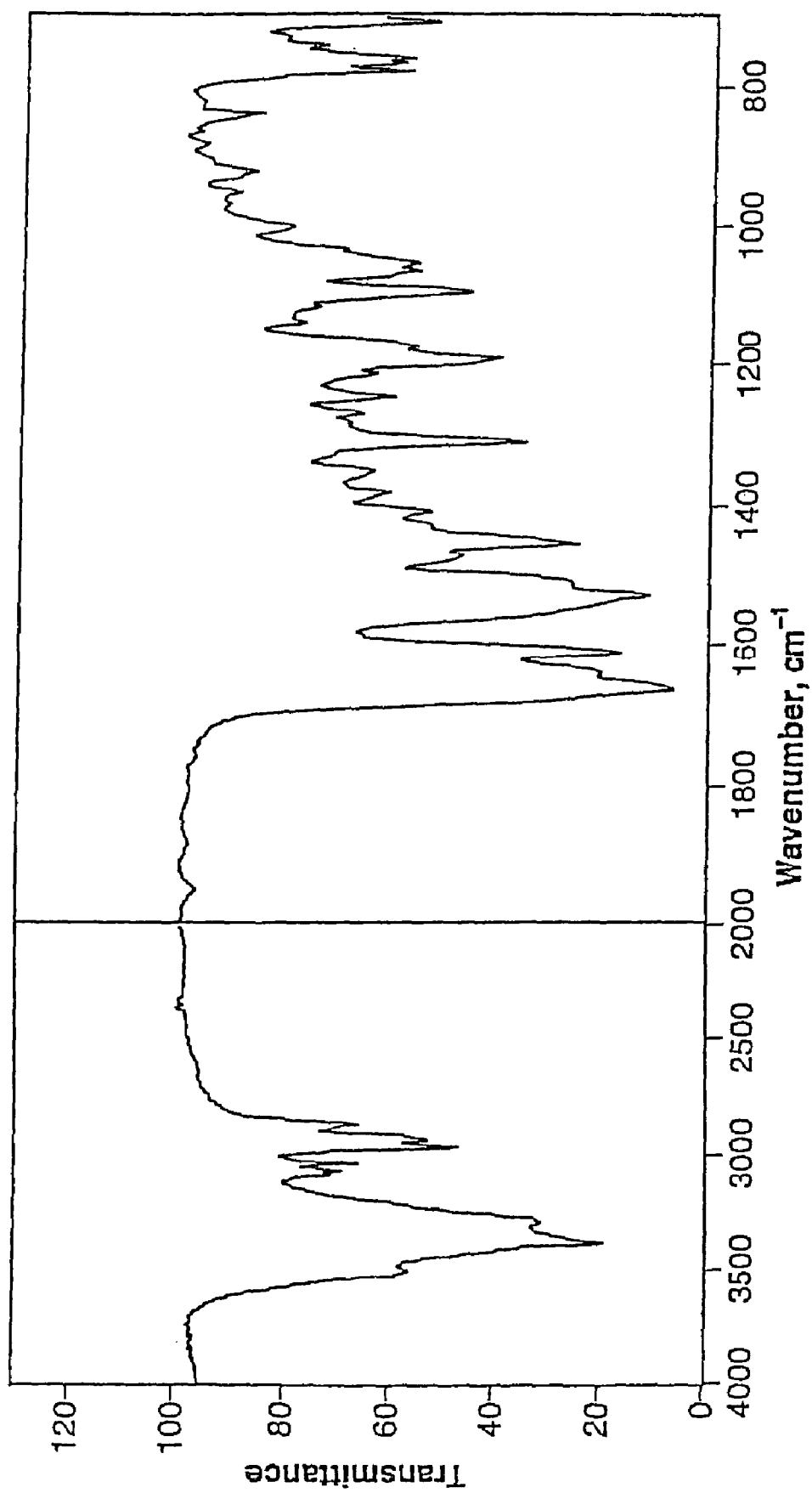
FIG. 8 is the solid state FT mid infrared spectrum of a Type I higher hydrated crystal form of lopinavir.

Lopinavir (30 g) was dissolved in a mixture of 360 mL of deionized distilled water and 418 mL of 190 proof ethanol by warming with moderate stirring at about 60° C. The hot solution was filtered by gravity to remove undissolved material. The filtrate was slowly cooled with gentle stirring to room temperature, at which point it was seeded with about 50 mg of the product of Example 1. The mixture was stirred at moderate speed at room temperature for three days. The resulting mixture was filtered under vacuum. The filtered solid was transferred onto a filter paper and any lumps were broken up with gentle manipulation with a spatula. The solid was then transferred to a glass crystallizing dish and placed in a desiccator over a saturated solution of sodium chloride, to maintain a constant 75% relative humidity. After drying for 12 days at room temperature (24±1° C.) and 75% relative humidity, about 20.5 g of the desired hydrated crystal form of lopinavir was obtained. Powder X-ray diffraction pattern (FIG. 5). 100 MHz solid state $^{13}$C nuclear magnetic resonance spectrum (FIG. 6). Solid state FT near IR (FIG. 7). Solid state FT mid-IR (FIG. 8). The product contained 4.3% volatile material by thermal gravimetry.

Example 4

Preparation of Type I Hydrated Crystal Form of Lopinavir Comprising about 0.5 Molecules of Water per Molecule of Lopinavir The product of Example 3 (about 100 mg) was loaded into the sample holder of a powder X-ray diffractometer fitted with a controlled atmosphere sample chamber and hot stage. The sample was warmed at 1° C./minute to 30° C. in an atmosphere of dry nitrogen and held at that temperature. Conversion to hemihydrate was complete within 60-90 minutes. Powder X-ray diffraction pattern (FIG. 1).

Example 5

Figure 2:
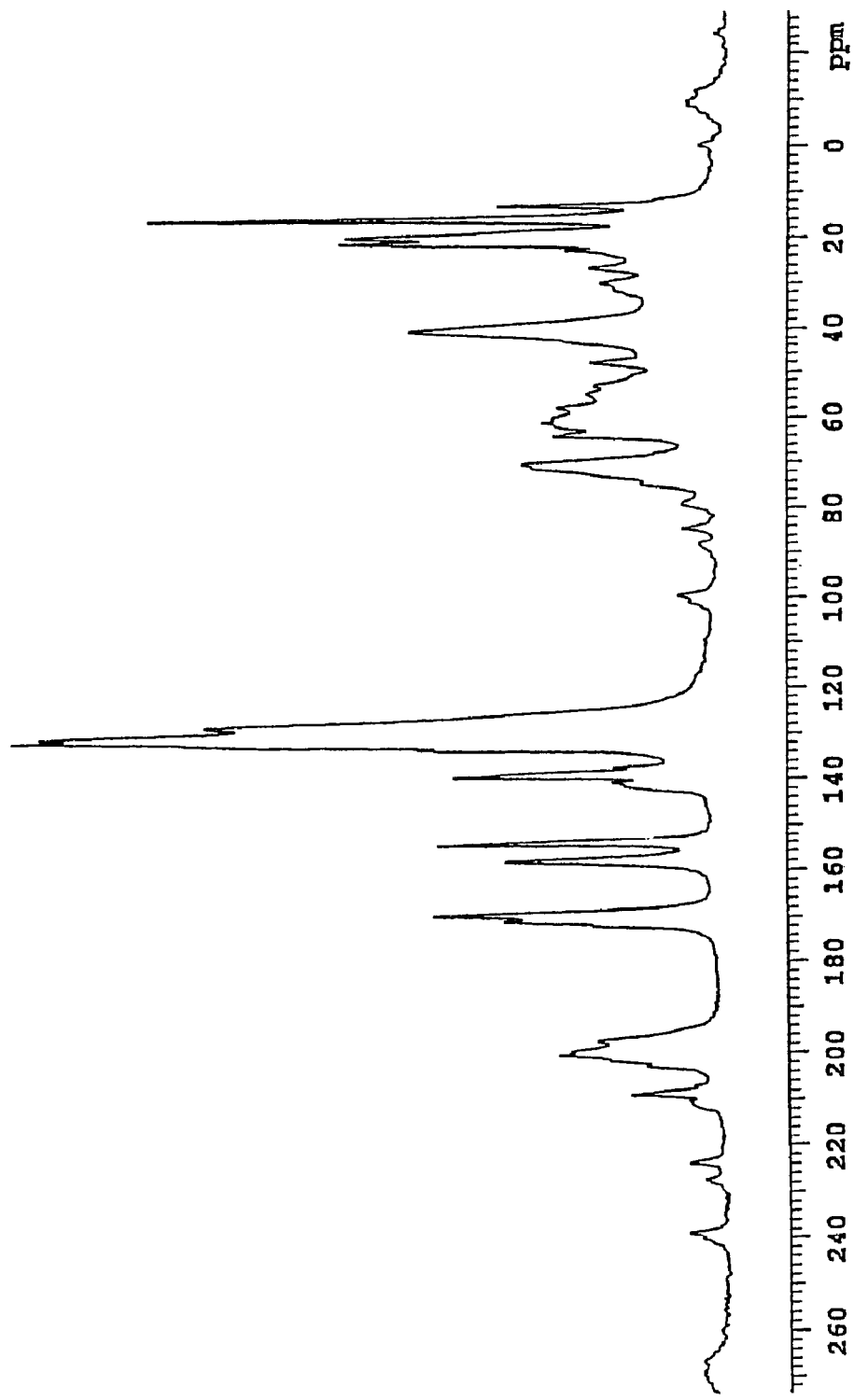
FIG. 2 is the 100 MHz solid state $^{13}C$ nuclear magnetic resonance spectrum of the Type I hydrated crystal form of lopinavir comprising about 0.5 molecules of water per molecule of lopinavir.
Figure 3:
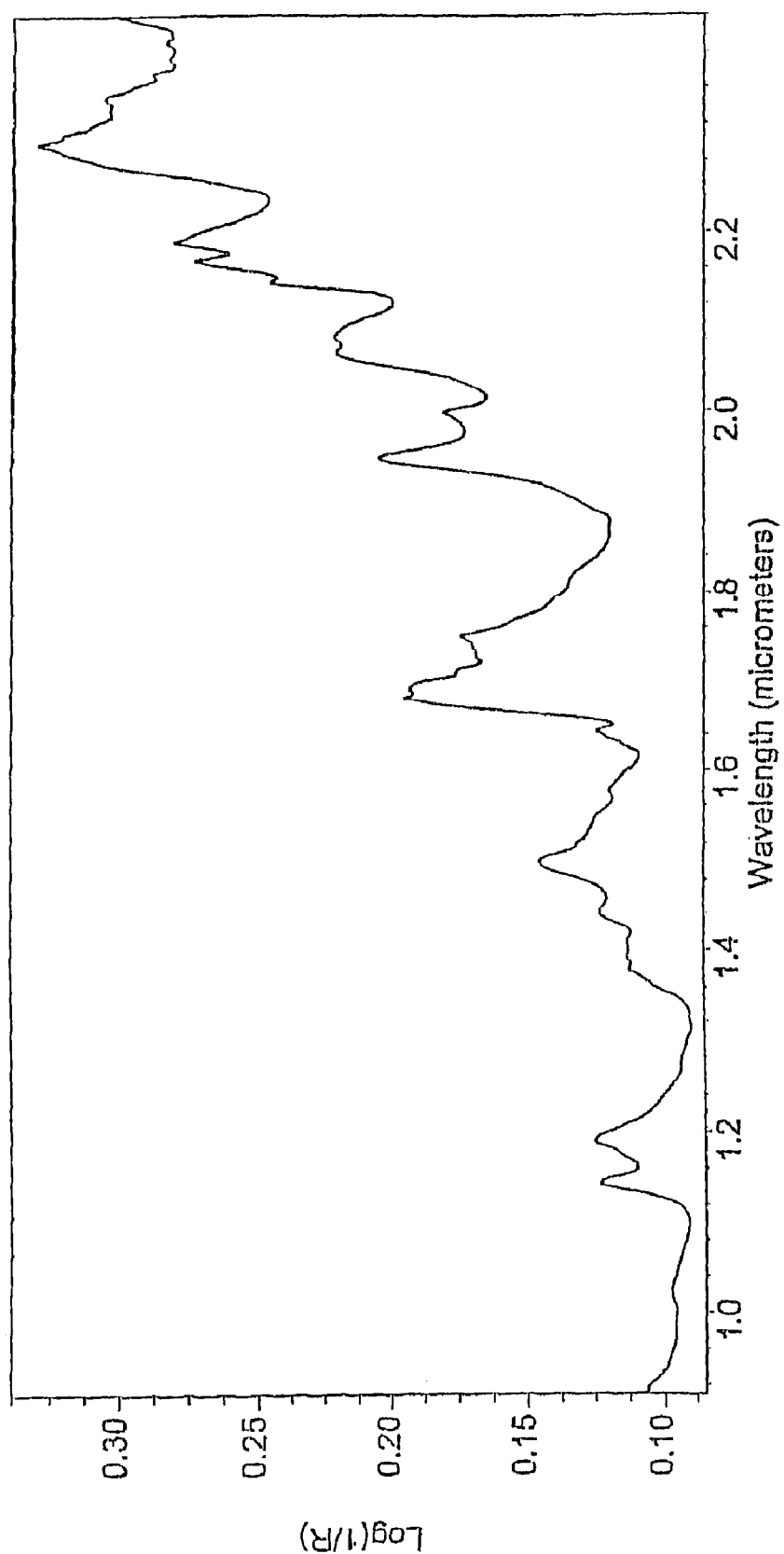
FIG. 3 is the solid state FT near infrared spectrum of the Type I hydrated crystal form of lopinavir comprising about 0.5 molecules of water per molecule of lopinavir.
Figure 4:
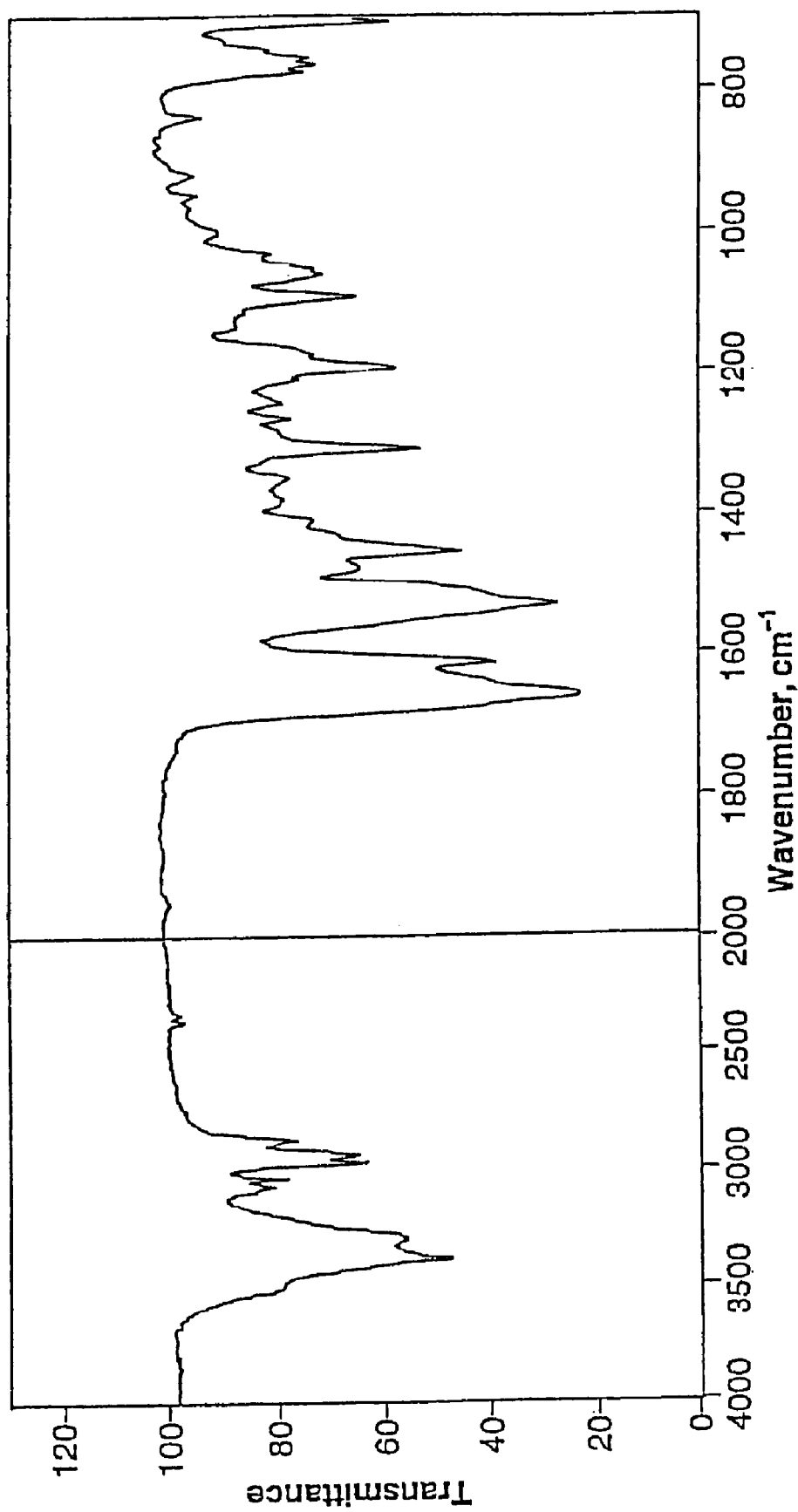
FIG. 4 is the solid state FT mid infrared spectrum of the Type I hydrated crystal form of lopinavir comprising about 0.5 molecules of water per molecule of lopinavir.

Preparation of Type I Hydrated Crystal Form of Lopinavir Comprising about 0.5 Molecules of Water per Molecule of Lopinavir The product of Example 3 (1 g) was spread as a thin layer in a polypropylene weigh boat and dried overnight in a vacuum oven at about −65 kPa at ambient temperature. The resultant hygroscopic product (hemihydrate of lopinavir) was transferred to glass vials and redried for 6 hours at about −65 kPa at ambient temperature. The vials were then quickly capped with polypropylene caps and stored in a desiccator over anhydrous calcium sulfate. 100 MHz solid state $^{13}C$ nuclear magnetic resonance spectrum (FIG. 2). Solid state FT near IR (FIG. 3). Solid state FT mid-IR (FIG. 4). The product contained 2% volatile material by thermal gravimetry.

Example 6

Preparation of Type II Isopropanol Hemisolvate Crystal Form of Lopinavir

Figure 9:
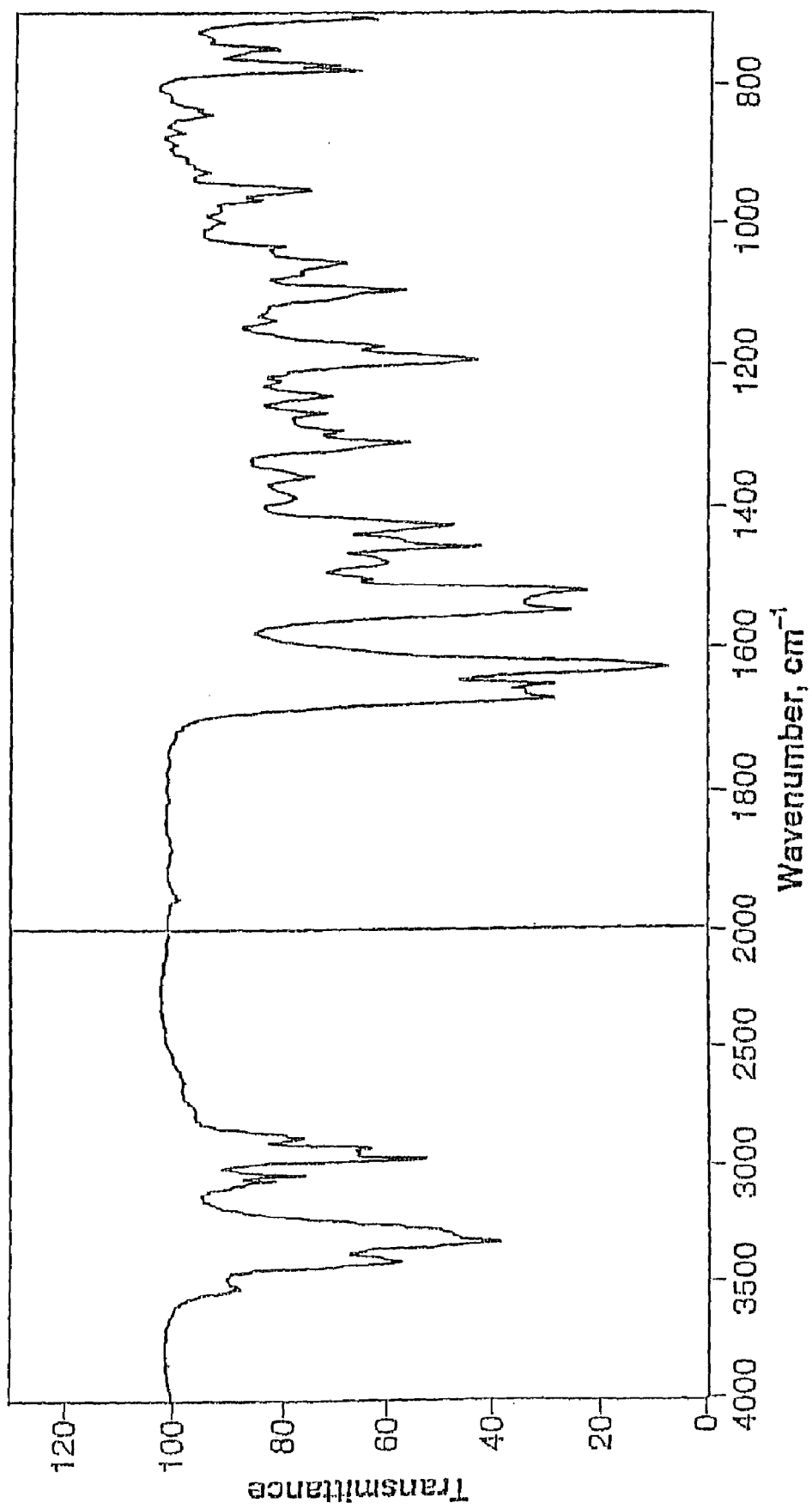
FIG. 9 is the solid state FT mid-infrared spectrum of the Type II isopropanol hemisolvate crystal form of lopinavir.
Figure 14:
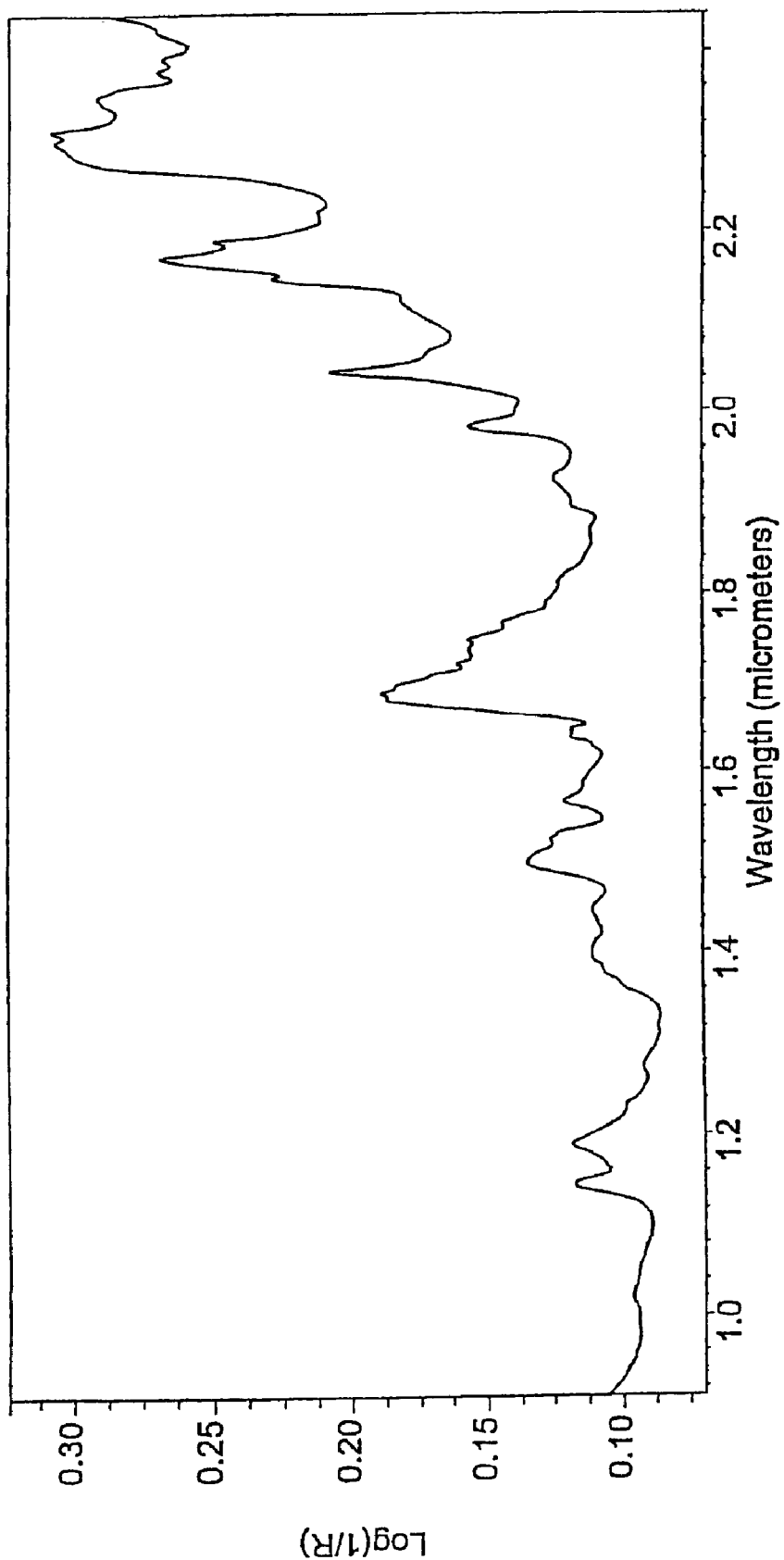
FIG. 14 is the solid state FT near infrared spectrum of the Type II isopropanol hemisolvate crystal form of lopinavir.

Lopinavir (16 g) was dissolved in 50 mL of isopropanol by heating the mixture on a hot plate to the boiling point with magnetic stirring. The solution was then cooled to room temperature and a precipitate formed. The resulting mixture was stirred at room temperature for 24 hours with just enough stirring to keep the precipitate suspended. The precipitate was collected by suction filtration and air dried to provide 9.9 g of the Type II isopropanol hemisolvate crystal form of lopinavir. Thermal gravimetry of the product indicated the presence of volatile material corresponding to 1 mole of isopropanol for every two moles of lopinavir. Powder X-ray diffraction analysis confirmed that the product was crystalline and infrared spectrometry confirmed that the product is the Type II solvated crystal form of lopinavir. Solid state FT mid-IR (FIG. 9). Solid state FT near IR (FIG. 14).

Example 7

Preparation of Type II Isopropanol Solvate Crystal Form of Lopinavir (1.6% Ispropanol by Weight by Thermal Gravimetry)

Lopinavir (1 g) was suspended in 2.5 mL of isopropanol in a glass vial containing four 4 mm diameter glass beads to promote mixing. The vial was capped and the suspension was tumbled end-over-end at room temperature for 4 months. The suspension was then transferred to a Petri dish and the solvent was allowed to evaporate slowly. The Petri dish was then placed in a vacuum oven, which was then warmed to 50° C. and the sample was dried at −65 kPa at 50° C. for 25 days to give the title compound. The product contained 1.6% volatile material by thermal gravimetry.

Example 8

Preparation of Type II Isopropanol Solvate Crystal Form of Lopinavir (2% Isopropanol by Weight by Thermal Gravimetry)

Figure 10:
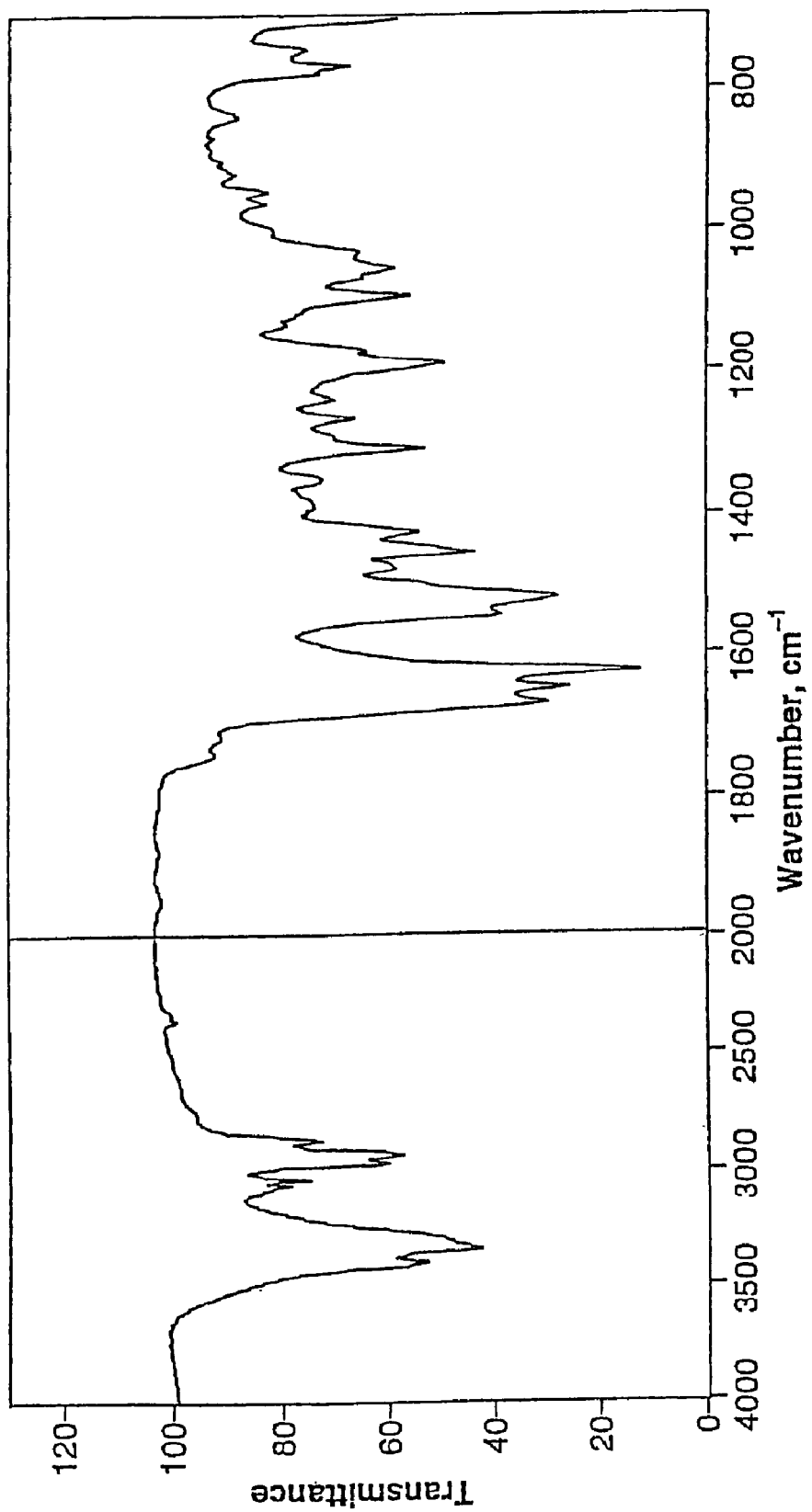
FIG. 10 is the solid state FT mid-infrared spectrum of the Type II isopropanol solvate crystal form of lopinavir having about 2% solvent by thermal gravimetry.
Figure 15:
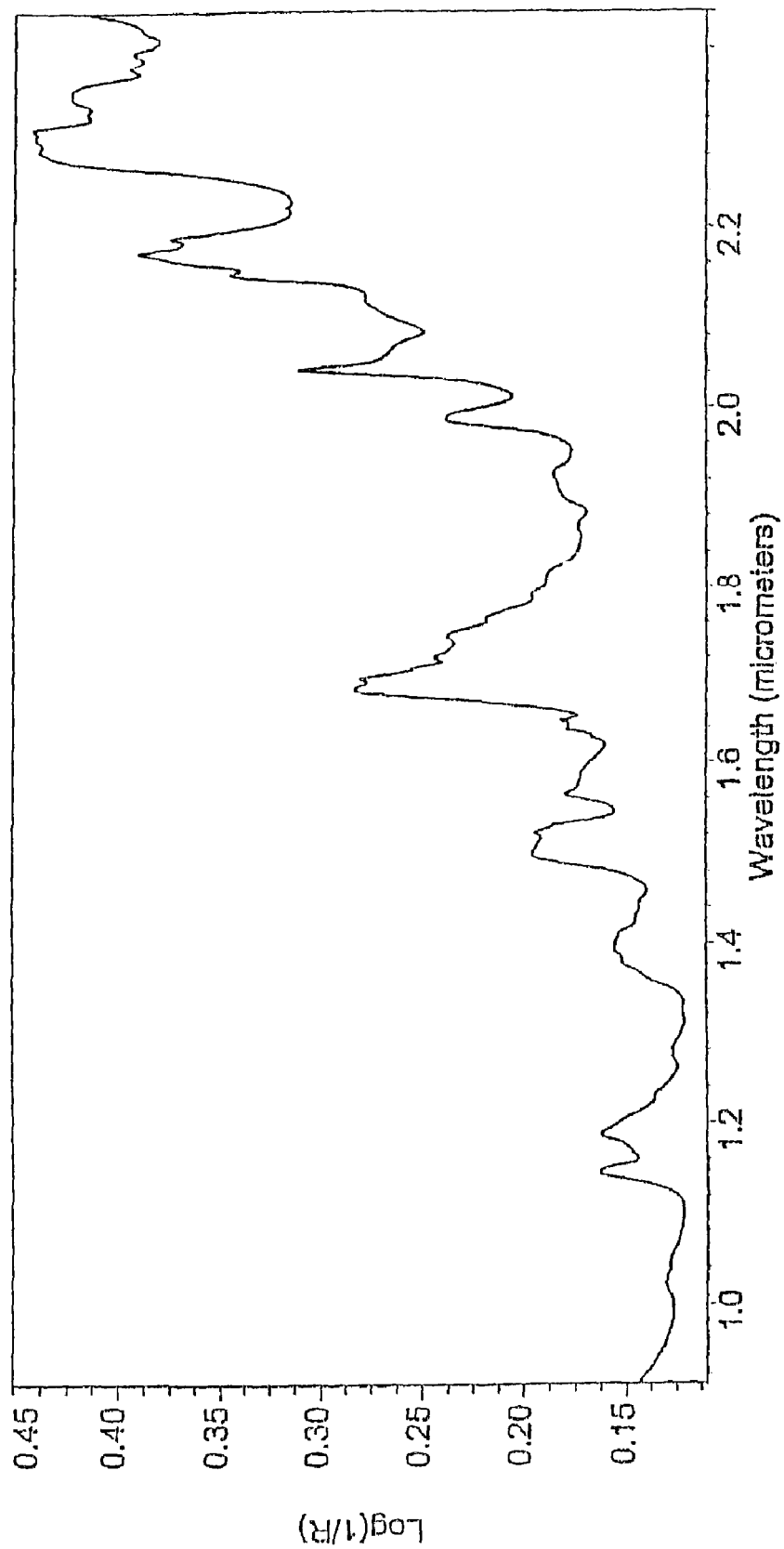
FIG. 15 is the solid state FT near infrared spectrum of the Type II isopropanol solvate crystal form of lopinavir having about 2% solvent by thermal gravimetry.

A sample of the product of Example 6 was rinsed with heptane, then dried for two day in a rotary evaporator. The residue was transferred to a Petri dish and dried in a vacuum oven, which was then warmed to 50° C. and the sample was dried at −65 kPa at 50° C. for 3 days to give the title compound. The product contained 2% volatile material by thermal gravimetry. Solid state FT mid-IR (FIG. 10). Solid state FT near IR (FIG. 15).

Example 9

Preparation of Type II Ethyl Acetate Hemisolvate Crystal Form Lopinavir

Example 9A

Preparation of Crude Lopinavir

Crude lopinavir, prepared according to U.S. Pat. No. 5,914,332 (Example 38) from (2S,3S,5S)-2-amino-3-hydroxy-5-[2S-(1-tetrahydropyrimid-2-onyl)-3-methylbutanoyl]amino-1,6-diphenylhexane (S)-pyroglutamic acid salt (about 85 g, corrected for solvent content), was dissolved in 318.5 grams of ethyl acetate and the solution was concentrated to an oil in vacuo. The residue was dissolved in 225 grams of ethyl acetate, then concentrated to an oil in vacuo twice. The residue was dissolved in ethyl acetate (approximately 300 mL) at 65° C., filtered to remove any trace undissolved solids, and concentrated to a foam in vacuo. The foam was dissolved in 338 grams of ethyl acetate and this solution was divided into four equal portions.

Example 9B

Preparation of Type II Ethyl Acetate Hemisolvate Crystal Form Lopinavir

Figure 11:
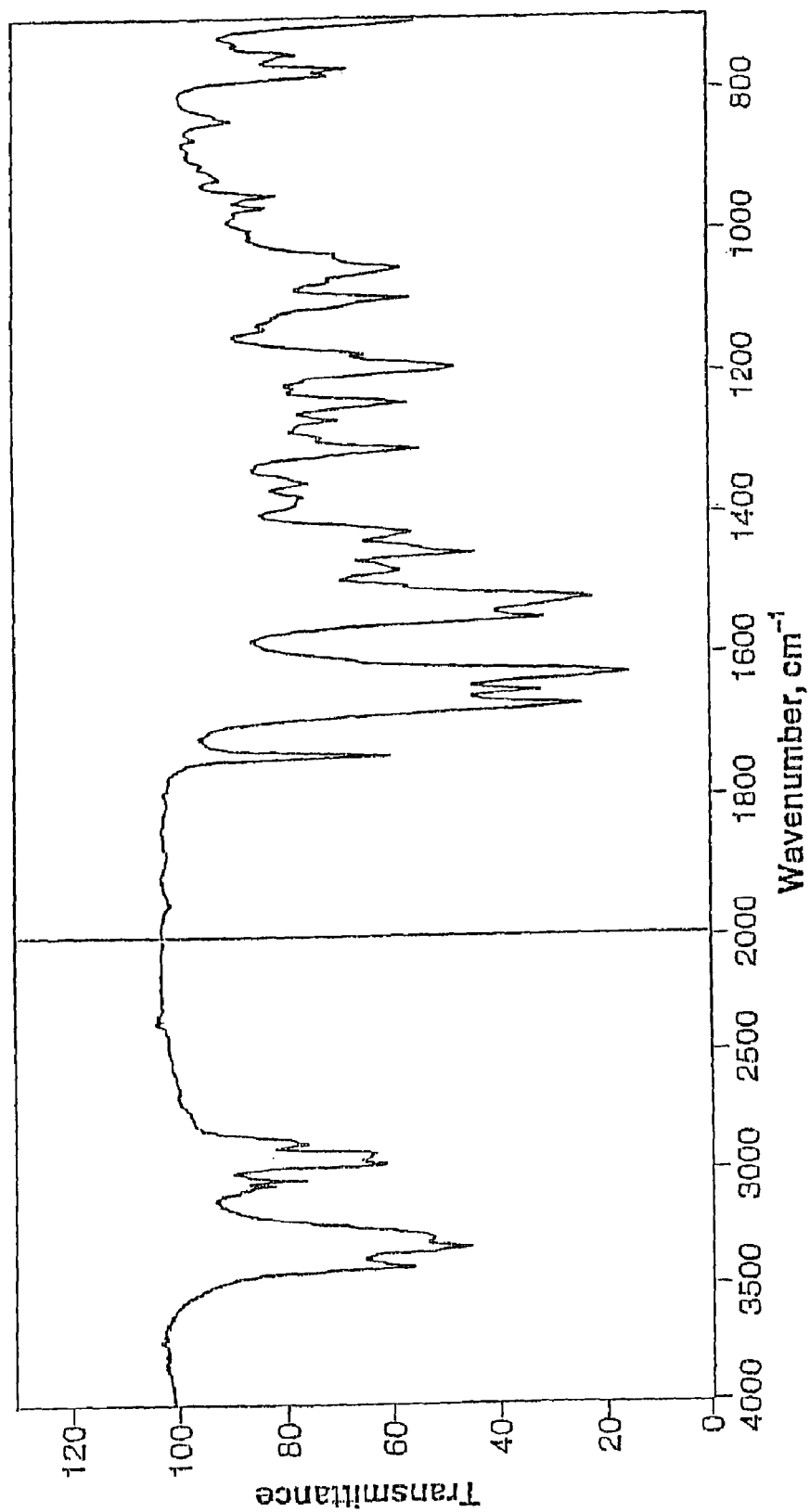
FIG. 11 is the solid state FT mid-infrared spectrum of the Type II ethyl acetate hemisolvate crystal form of lopinavir.
Figure 16:
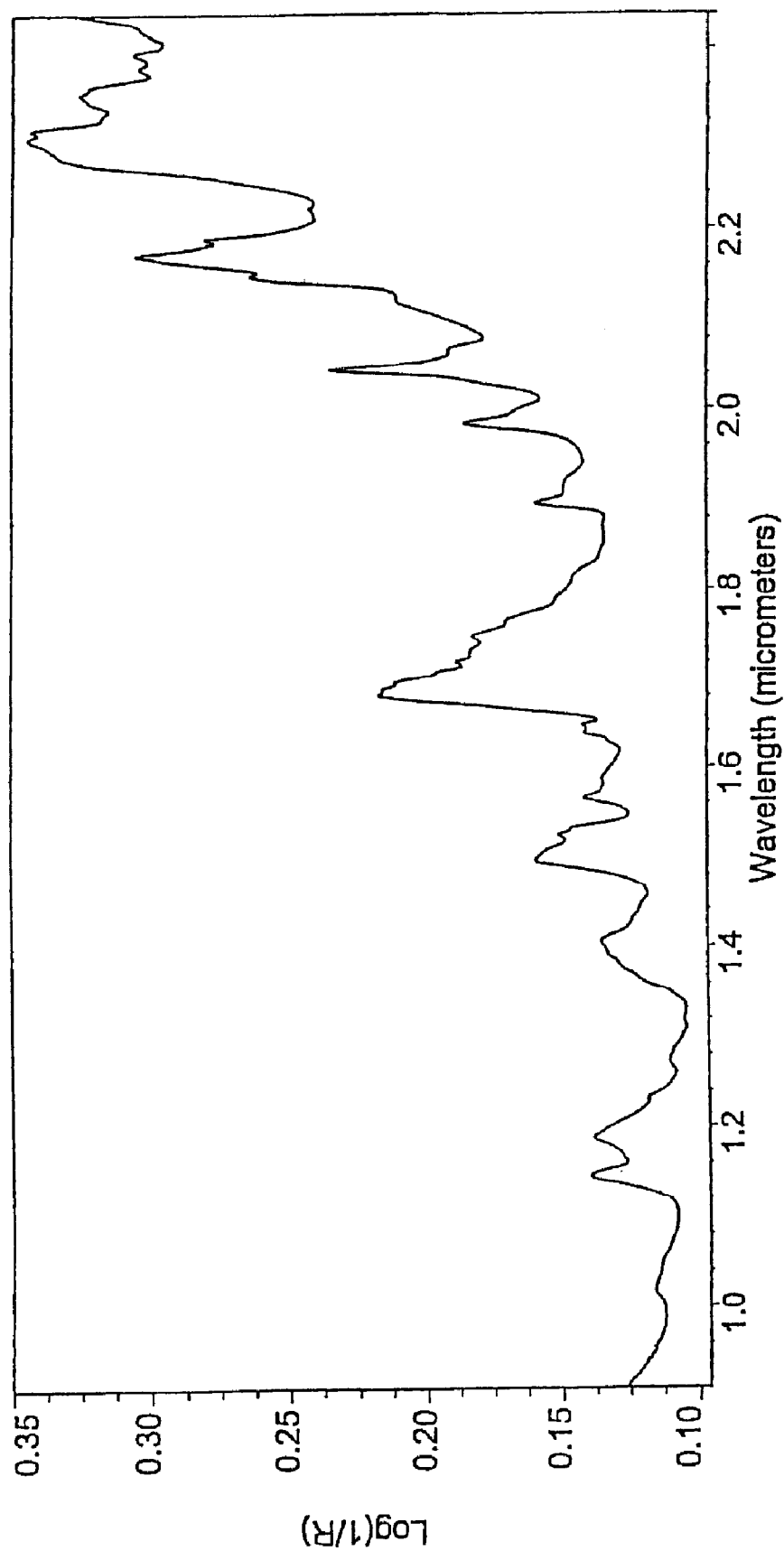
FIG. 16 is the solid state FT near infrared spectrum of the Type II ethyl acetate hemisolvate crystal form of lopinavir.

One portion of the lopinavir solution prepared in Example 9A was concentrated to an oil in vacuo, then dissolved in 50 mL absolute ethanol. Solvent was removed in vacuo. The residue was maintained under vacuum with heating (approximately 55-60° C.) for an additional 30 minutes. The resulting foam was dissolved in ethyl acetate (87 mL) at ambient temperature. In less than five minutes of mixing, solids were evident. The resulting slurry was mixed for 16 hours, then diluted with 87 mL of heptanes. After three hours the solids were collected by filtration, washed with 36 mL EtOAc/heptanes (1:1 v/v), and dried under vacuum at 60° C. for 72 hours, affording 19.4 grams of the Type II ethyl acetate hemisolvate of lopinavir. Solid state FT mid-IR (FIG. 11). Solid state FT near IR (FIG. 16). The product contained 4.4% volatile material by thermal gravimetry.

Example 9C

Alternative Preparation of Type II Ethyl Acetate Hemisolvate Crystal Form Lopinavir Crude lopinavir, prepared according to U.S. Pat. No. 5,914,332 (Example 38) from (2S,3S,5S)-2-amino-3-hydroxy-5-[2S-(1-tetrahydropyrimid-2-onyl)-3-methylbutanoyl]amino-1,6-diphenylhexane (s)-pyroglutamic acid salt (about 20 g, corrected for solvent content), was dissolved in 118 grams of ethyl acetate and was then concentrated to an oil in vacuo. The residue was dissolved in 95.7 grams of ethyl acetate at 46° C., then concentrated to an oil in vacuo. The residue was dissolved in 95.8 grams ethyl acetate at 64° C. Measurement for moisture by KF showed less than 0.05% water. The product solution was cooled to 41° C. and seeded with 0.20 grams of the product of Example 9B. The solution was cooled to 35° C. and mixed at that temperature for 1.25 hours. The resulting slurry was then cooled to 15° C. over 10 minutes, and mixed at 15-18° C. for 1.5 hours. The solids were collected by filtration, washed with 13.3 grams of ethyl acetate, and dried under vacuum at 56-58° C. for 16 hours, affording 12.3 grams of the Type II ethyl acetate hemisolvate of lopinavir Example 10A Preparation of Type II Ethyl Acetate Solvate Crystal Form Lopinavir (Having Less than 0.5 moles of Ethyl Acetate per 2 moles of Lopinavir by Thermal Gravimetry)

Figure 12:
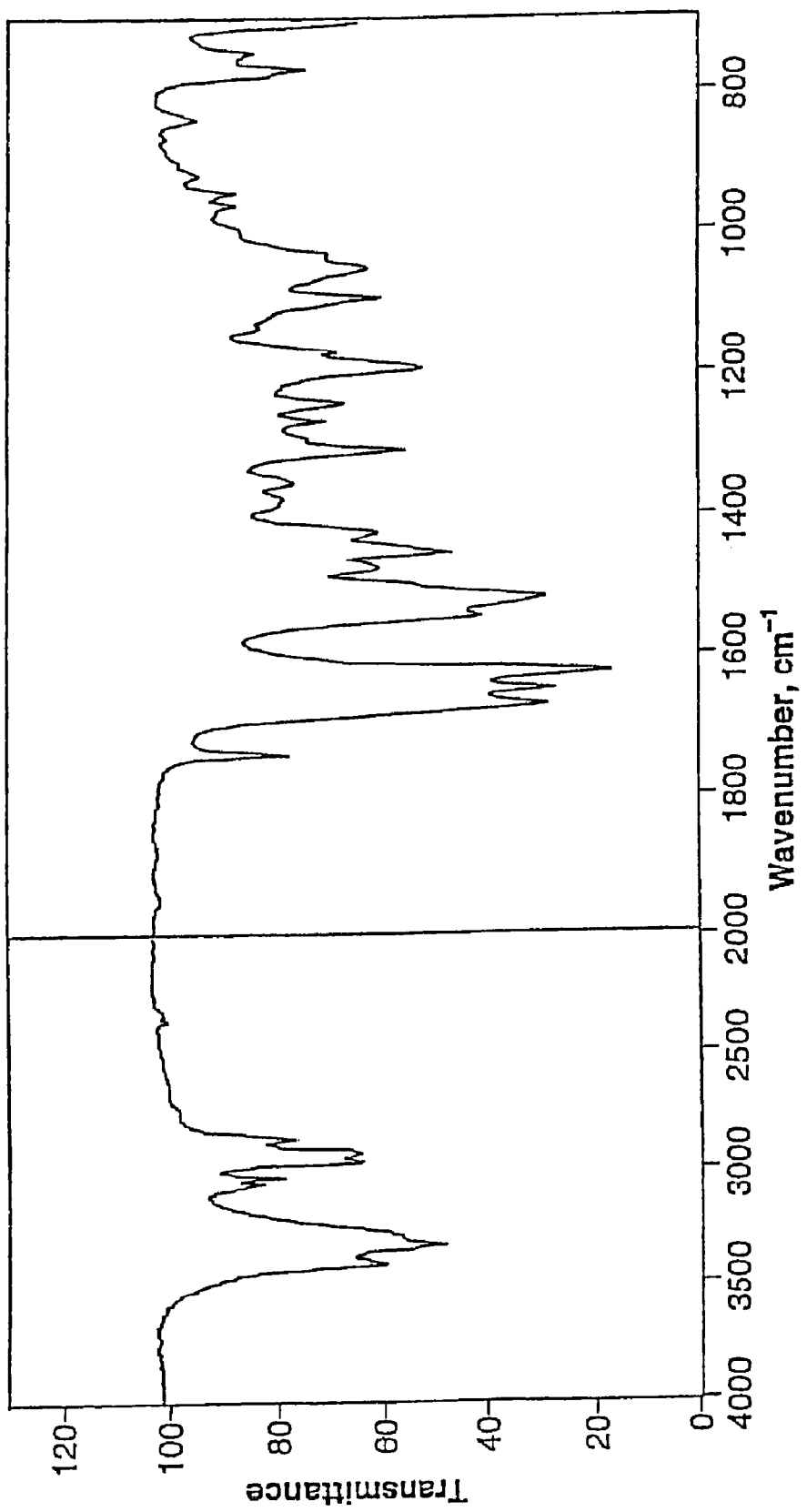
FIG. 12 is the solid state FT mid-infrared spectrum of the Type II ethyl acetate solvate crystal form of lopinavir having less than 0.5 moles of ethyl acetate per 2 moles of lopinavir by thermal gravimetry.
Figure 17:
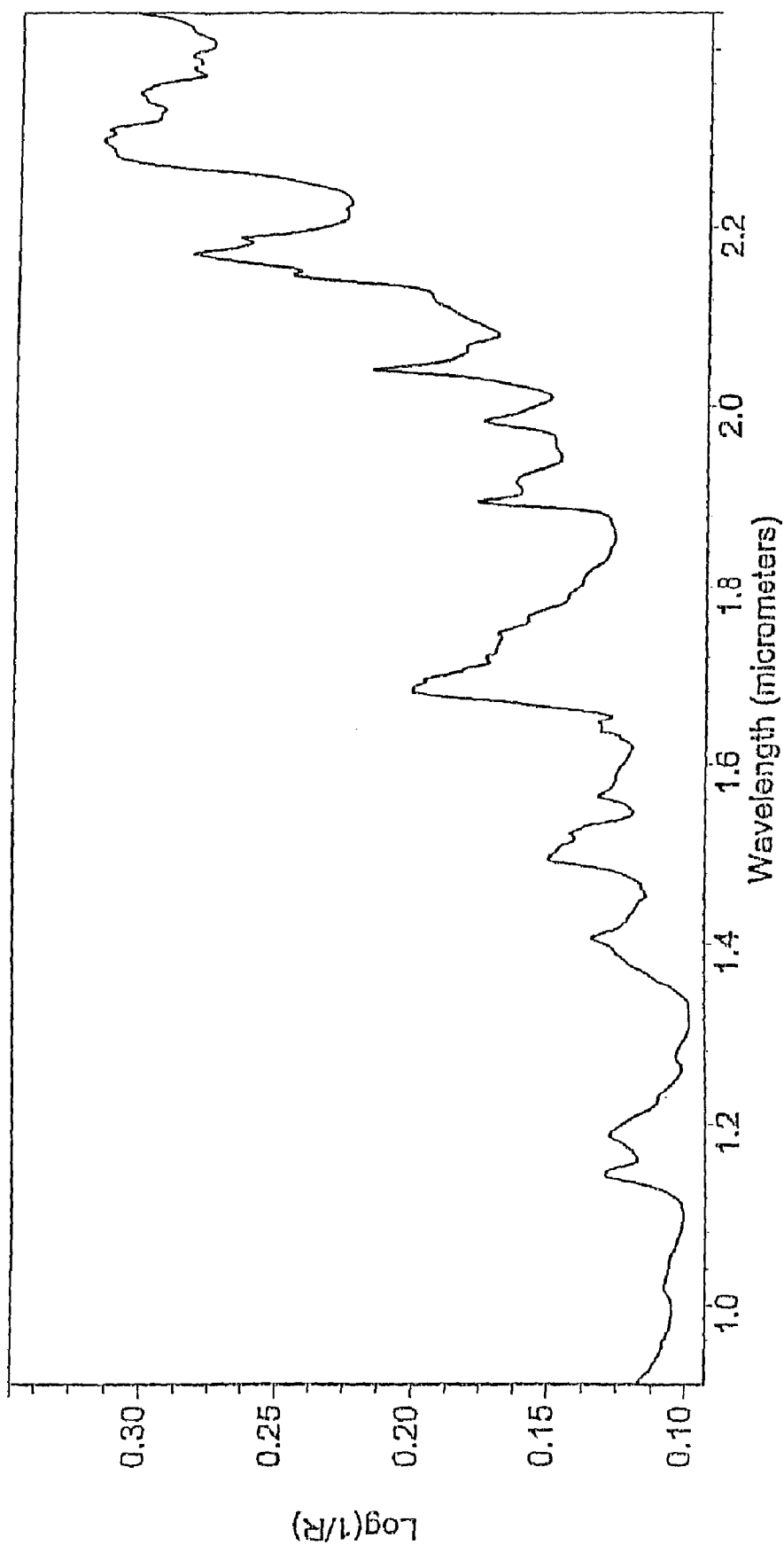
FIG. 17 is the solid state FT near infrared spectrum of the Type II ethyl acetate solvate crystal form of lopinavir having less than 0.5 moles of ethyl acetate per 2 moles of lopinavir by thermal gravimetry.

One portion of the lopinavir solution prepared in Example 9A was concentrated to an oil in vacuo, then dissolved in 50 mL of absolute ethanol. Solvent was removed in vacuo. The residue was maintained under vacuum with heating (approximately 55-60° C.) for an additional 30 minutes. Seed crystals of the product of Example 9B were added to the resulting foam. The foamy residue was then dissolved in ethyl acetate (87 mL) at ambient temperature. In less than five minutes of mixing, solids were evident. The resulting slurry was mixed for 16 hours, then diluted with 87 mL of heptanes. After three hours, the solids were collected by filtration, washed with 36 mL of EtOAc/heptanes (1:1 v/v), and dried under vacuum at 60° C. for 72 hours, affording 19.37 grams of the Type II ethyl acetate solvate of lopinavir. Solid state FT mid-IR (FIG. 12). Solid state FT near IR (FIG. 17). The product contained 1.7% volatile material by thermal gravimetry.

Example 10B

Alternative Preparation of Type II Ethyl Acetate Solvate Crystal Form Lopinavir (Having Less than 0.5 Moles of Ethyl Acetate Per 2 Moles of Lopinavir by Thermal Gravimetry)

A solution of crude lopinavir prepared according to U.S. Pat. No. 5,914,332 (Example 2; coupling of 17.0 g of (2S,3S,5S)-2-(2,6-dimethylphenoxyacetyl)amino-3-hydroxy-5-amino-1,6-diphenylhexane with 8.0 g of 2S-(1-tetrahydropyrimid-2-onyl)-3-methylbutanoic acid via EDAC/HOBT coupling) in isopropyl acetate (about 250 mL) was concentrated to an oil in vacuo. The residue was dissolved in 250 mL of ethyl acetate and concentrated to a foam in vacuo. The foam was dissolved in 120 mL of warm ethyl acetate. The solution was divided into three portions of 44.9 grams each. The solutions were cooled to ambient temperature after which crystallization occurred rapidly. One of those portions was mixed at ambient temperature overnight. The solids were collected by filtration, washed with 8 ml of ethyl acetate, then dried under vacuum at 22° C. for 40 hours, then dried an additional 44 hours under vacuum at 70° C. affording 6.23 grams grams of the Type II ethyl acetate solvate of lopinavir.

Example 11

Preparation of Type II Chloroform Hemisolvate Crystal Form Lopinavir

Figure 13:
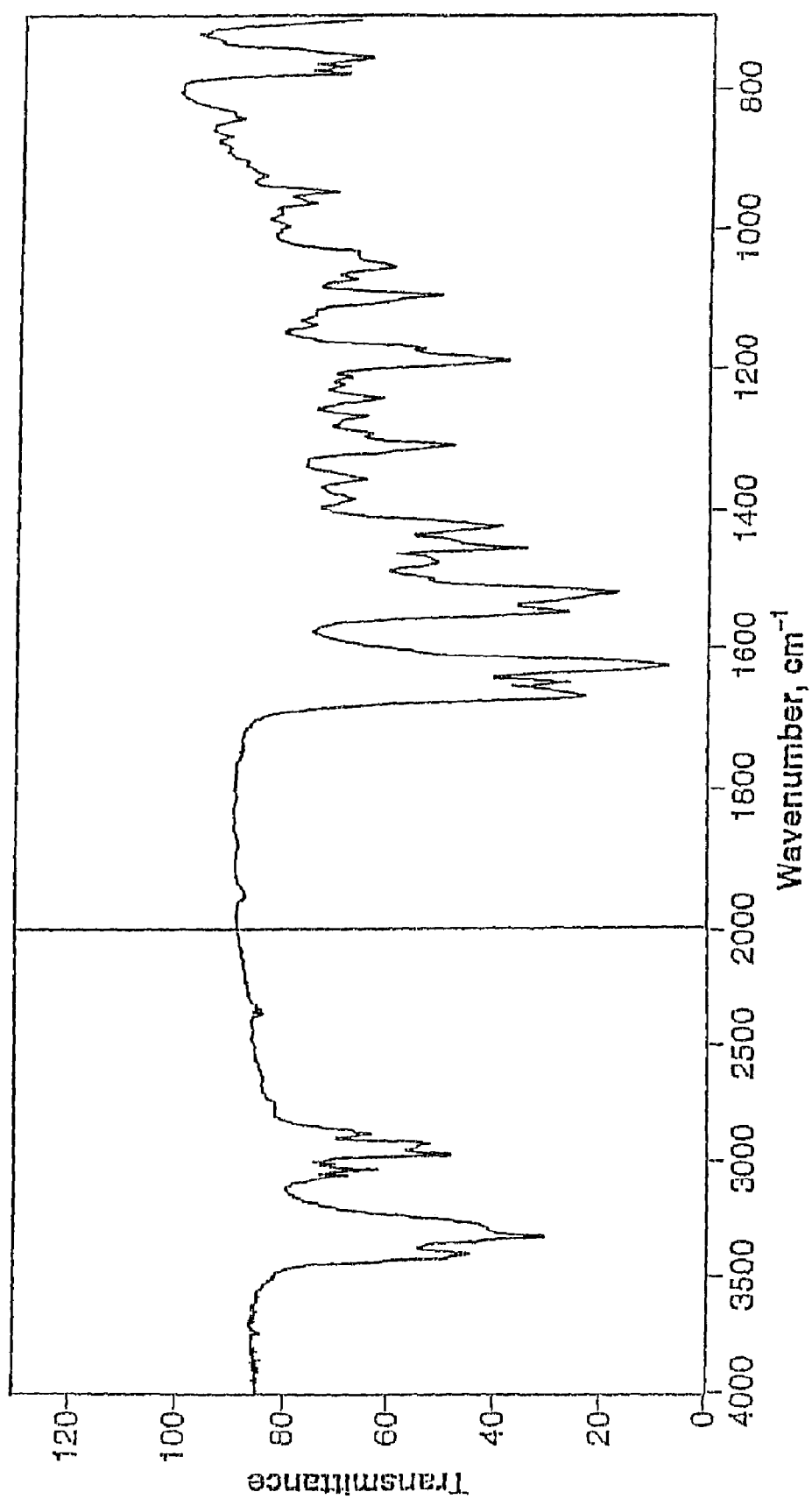
FIG. 13 is the solid state FT mid-infrared spectrum of the Type II chloroform hemisolvate crystal form of lopinavir.
Figure 18:
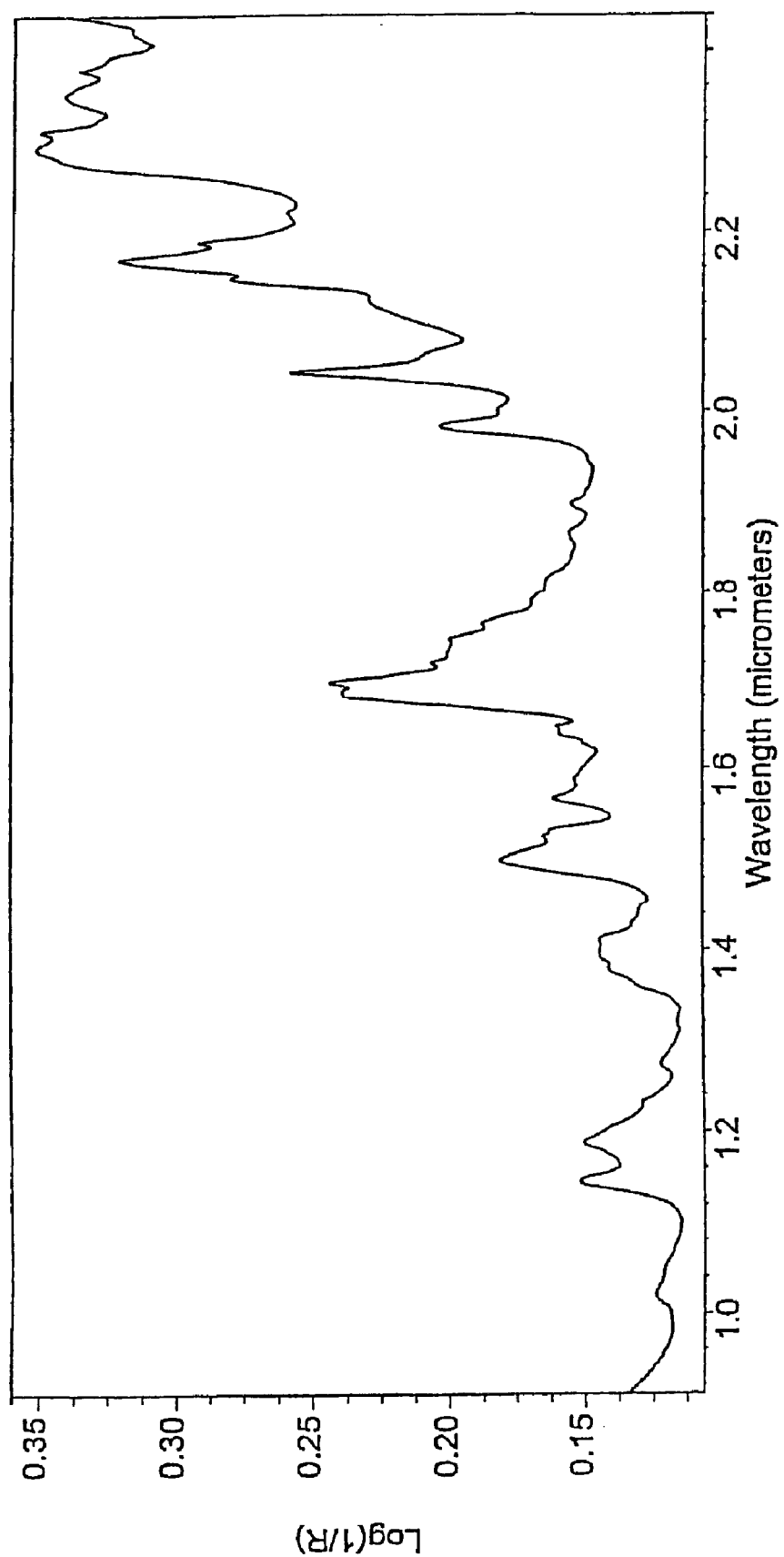
FIG. 18 is the solid state FT near infrared spectrum of the Type II chloroform hemisolvate crystal form of lopinavir.

Lopinavir (10 g) was dissolved in 30 mL of chloroform. The solution was then heated to boiling on a hot plate with magnetic stirring. After reducing the volume of the solution to about ½ of the initial volume, about 10 mL of n-heptane was added dropwise until the solution started to become turbid. Then about 30 mL more of chloroform was added and boiling was continued until the volume was again about ½ of the original volume. Then about 20 mL of chloroform was added and boiling was continued until the volume was again about ½ of the original volume. The mixture was then cooled slowly to room temperature and allowed to partially evaporate. After the slow evaporation, a glassy residue with the consistency of molasses remained. This was mixed with about 20 mL of chloroform and warmed on a hot plate. Then n-heptane was added dropwise until a precipitate began to form. The precipitate was dissolved by rewarming of the mixture. The warm solution was transferred to a beaker, which was placed inside a jar containing about 20 mL of heptane, and allowed to cool. After about 1 hour a thick solid precipitate formed. Most of the precipitate was redissolved by adding about 20 mL of chloroform to the contents of the beaker. After letting this mixture stand for about 1 hour, a few needle shaped crystals formed. More heptane (about 40 mL) was added to the jar containing the beaker and the jar was capped and allowed to stand. After one day, the beaker contained large numbers of crystals. The crystals were collected by vacuum filtration. The crystal mass was broken up gently using a spatula and the crystals were washed with the chloroform/heptane mixture from the jar external to the beaker in which the crystals had been grown. Thermal gravimetry of the product indicated the presence of volatile material corresponding to 1 mole of chloroform for every two moles of lopinavir. Powder X-ray diffraction analysis confirmed that the product was crystalline and infrared spectrometry confirmed that the product is the Type II solvated crystal form of lopinavir. Solid state FT mid-IR (FIG. 13). Solid state FT near IR (FIG. 18).

Example 12

Preparation of Type III Ethyl Acetate Solvated Crystal Form Lopinavir

Figure 20:
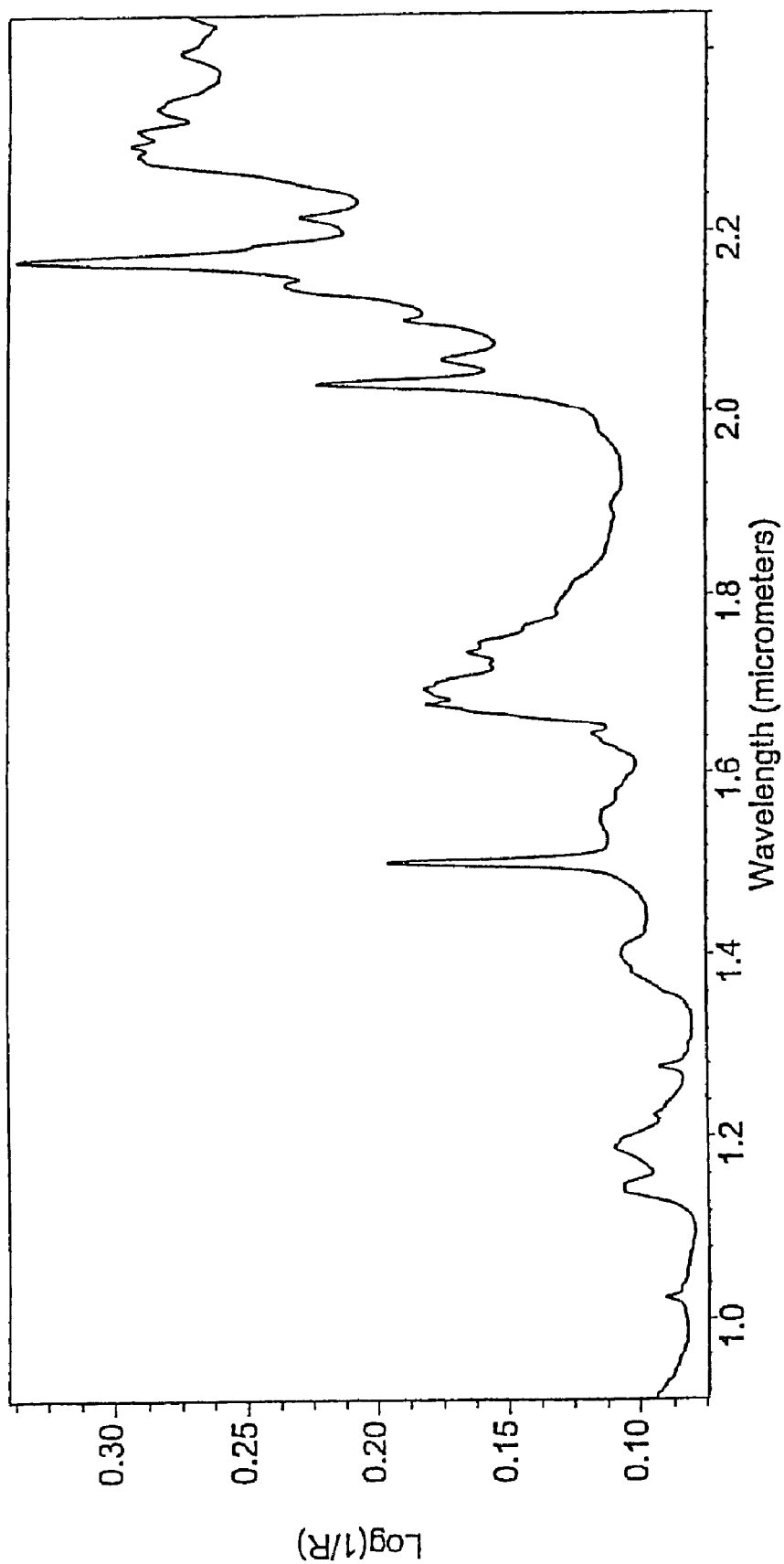
FIG. 20 is the solid state FT near infrared spectrum of the Type III ethyl acetate solvated crystal form of lopinavir.

Lopinavir (7.03 g) was dissolved in ethyl acetate (33.11 g) at 71° C. The solution was cooled to 42° C. over 45 minutes, at which point solids were evident. The slurry was cooled to 35° C. over 30 minutes, then mixed for one hour. Then the slurry was cooled to 15° C. over 13 minutes and then mixed for one hour. Mixed heptanes (25.1 g) were added dropwise over 13 minutes. The resulting slurry was mixed for 30 minutes. The resulting solids were collected by filtration, washed with ethyl acetate/mixed heptanes (1:1 v/v, 20 mL) and dried under vacuum at 62° C. for 20 hours to give 6.4 g of the title compound. Powder X-ray diffraction analysis confirmed that the product was crystalline and infrared spectrometry confirmed that the product is the Type III solvated crystal form of lopinavir. Solid state FT mid-IR (FIG. 19). Solid state FT near IR (FIG. 20). The product contained 2.3% volatile material by thermal gravimetry.

Example 13

Preparation of Type III Ethyl Acetate Solvated Crystal Form of Lopinavir

Approximately 100 mg of lopinavir was dissolved in about 3 mL of ethyl acetate. To this solution was slowly and carefully added about 3 mL of heptane. After standing, crystals of the Type III solvated crystal form of lopinavir grew by liquid diffusion crystallization.

Example 14

Preparation of Type III Ethyl Acetate Solvated Crystal Form of Lopinavir

One portion of the lopinavir solution prepared in Example 9A was diluted with 14.8 grams of ethyl acetate and heated to 70-75° C., then diluted with 75 grams of heptanes while maintaining an internal temperature greater than 70° C. The resulting solution was heated to 75° C. for 15 minutes, then allowed to cool to ambient temperature gradually. After mixing overnight at ambient temperature the solids were collected by filtration, washed with 36 mL of ethyl acetate/heptanes (1:1 v/v), and dried under vacuum at 60° C. for 72 hours, affording 21.5 grams of the title compound.

Example 15

Preparation of Type III Desolvated Crystal Form of Lopinavir

Figure 22:
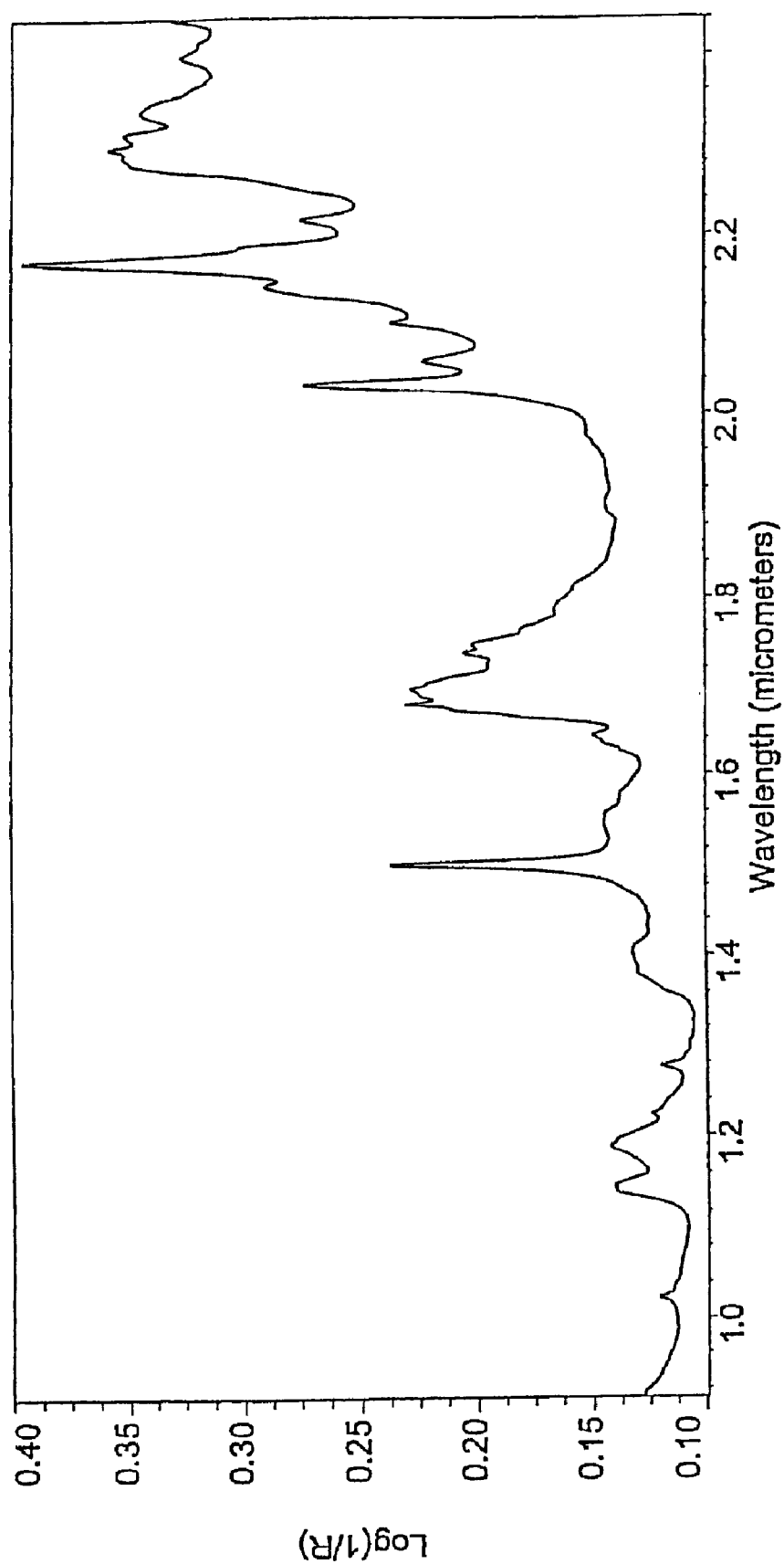
FIG. 22 is the solid state FT near infrared spectrum of the Type III desolvated crystal form of lopinavir.
Figure 24:
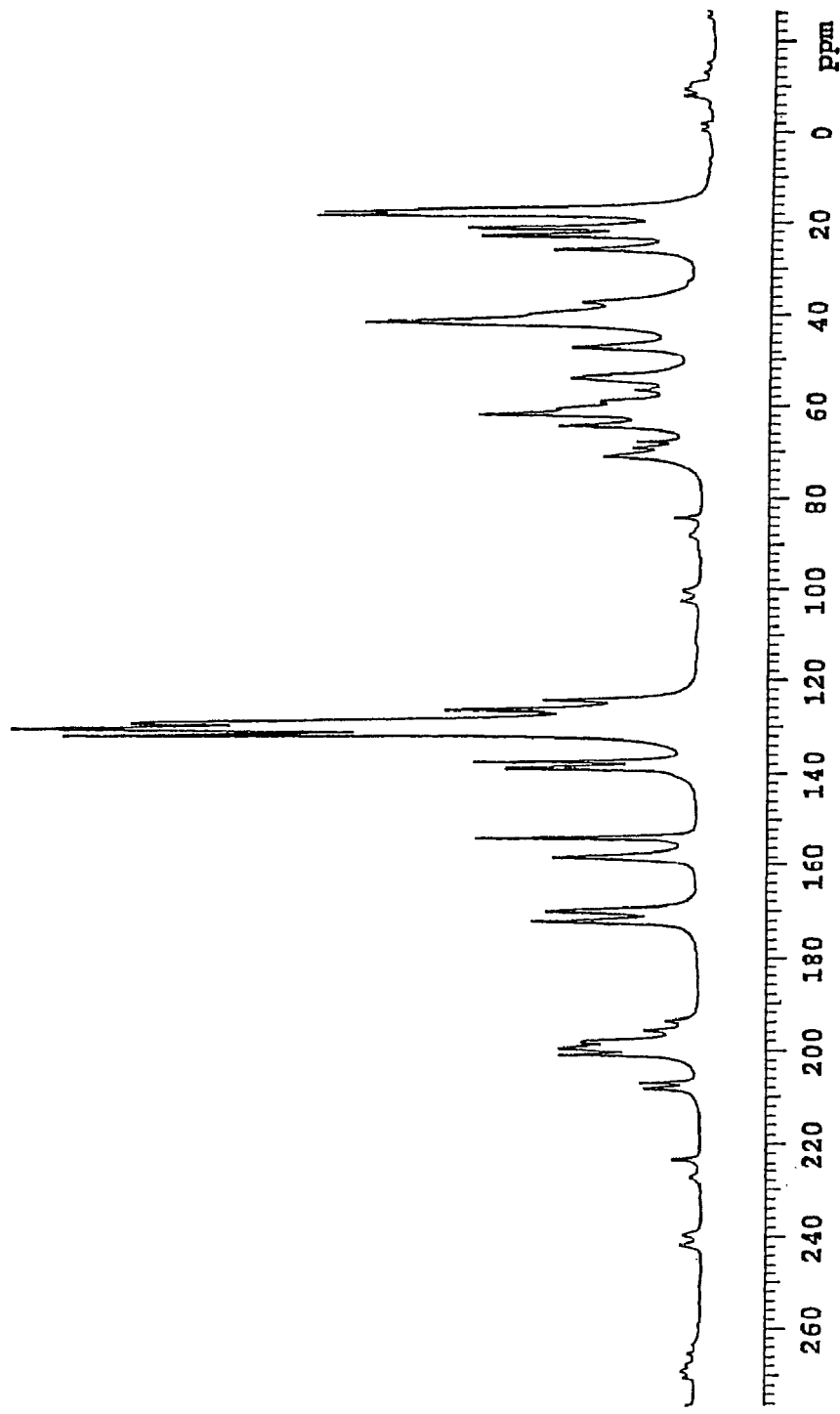
FIG. 24 is the 100 MHz solid state $^{13}$C nuclear magnetic resonance spectrum of the Type III desolvated crystal form of lopinavir.
Figure 25:
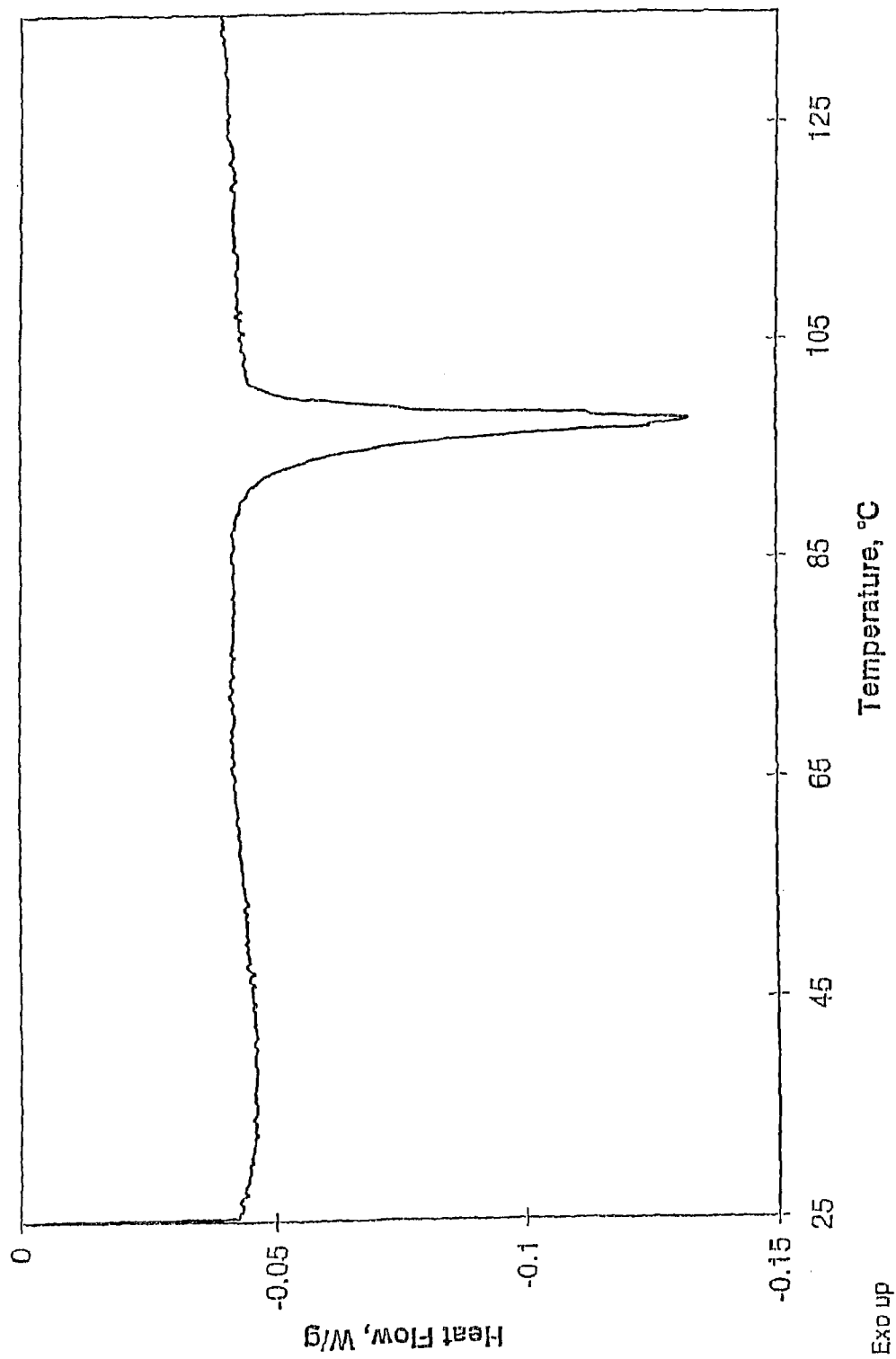
FIG. 25 is the differential scanning calorimetric (DSC) thermogram for the Type III desolvated crystal form of lopinavir.

Lopinavir (5 g) was placed in a 100 mL beaker. Just enough acetonitrile was added to dissolve approximately 95% of the lopinavir. Some needle-shaped crystals remained undissolved. The beaker was placed inside a jar containing about a 1 cm deep layer of anhydrous calcium sulfate (DRIERITE). The jar was capped and the material was left undisturbed at ambient temperature. After standing overnight, a large amount of white crystalline material had precipitated. The supernatant (about 6 mL) was decanted from the beaker. Fresh acetonitrile (3-4 mL) was added to the precipitate, which was then gently broken up with a spatula. The solid was collected by suction filtration and rinsed with about 1 mL of acetonitrile. The solid was transferred to a Petri dish and dried under vacuum at ambient temperature to give the Type III desolvated crystal form of lopinavir. Powder X-ray diffraction analysis confirmed that the product was crystalline and infrared spectrometry confirmed that the product is the Type III crystal form of lopinavir. The product contained less than 0.05% volatile material by thermal gravimetry. Solid state FT mid-IR (FIG. 21). Solid state FT near IR (FIG. 22). Powder X-ray diffraction pattern (FIG. 23). 100 MHz solid state $^{13}C$ nuclear magnetic resonance spectrum (FIG. 24). DSC thermogram (FIG. 25).

Example 16

Preparation of Type IV Non-Solvated Crystal Form of Lopinavir

Lopinavir (amorphous, 1 g) was placed in a crystallizing dish (A). This dish was placed in a bigger crystallizing dish (B) containing about 10 mL of acetonitrile and sitting on a hot plate. An intermediate size crystallizing dish (C) was inverted and placed over dish A, but still inside of dish B. A large crystallizing dish (D) was inverted and placed over dishes A, B and C. The hot plate was warmed to about 35° C. and then the hot plate was turned off. The whole assembly was then allowed to sit for 10 days at ambient temperature. After 10 days, all of the acetonitrile had evaporated.

A portion of the resulting crystalline product (0.1 g) was mixed with acetonitrile (0.6 mL) and stirred for 1 hour. The mixture was filtered and the solid allowed to air dry to give the Type IV non-solvated crystal form of lopinavir.

Example 17

Preparation of Type IV Non-Solvated Crystal Form of Lopinavir

Figure 26:
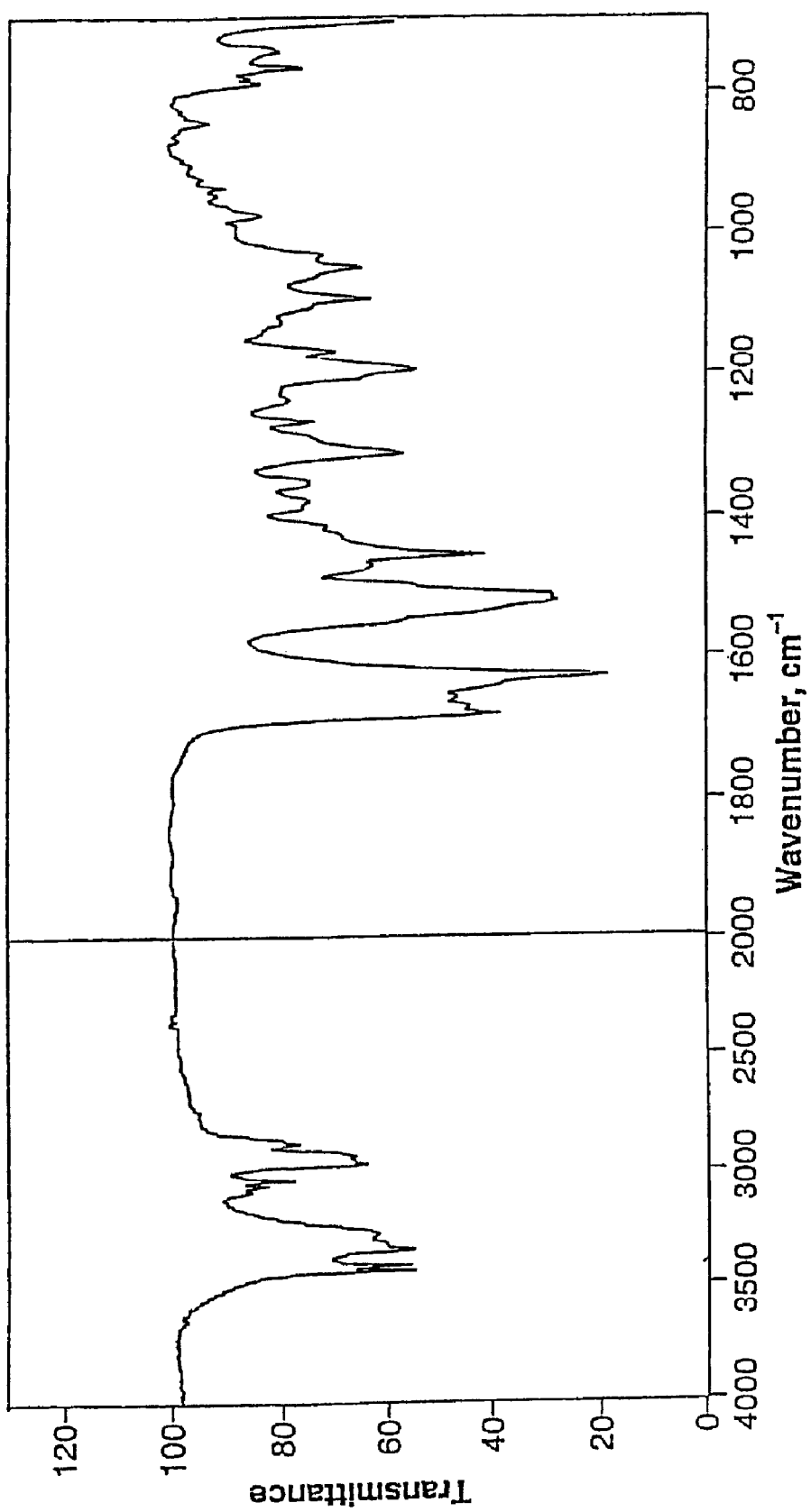
FIG. 26 is the solid state FT mid-infrared spectrum of the Type IV non-solvated crystal form of lopinavir.
Figure 27:
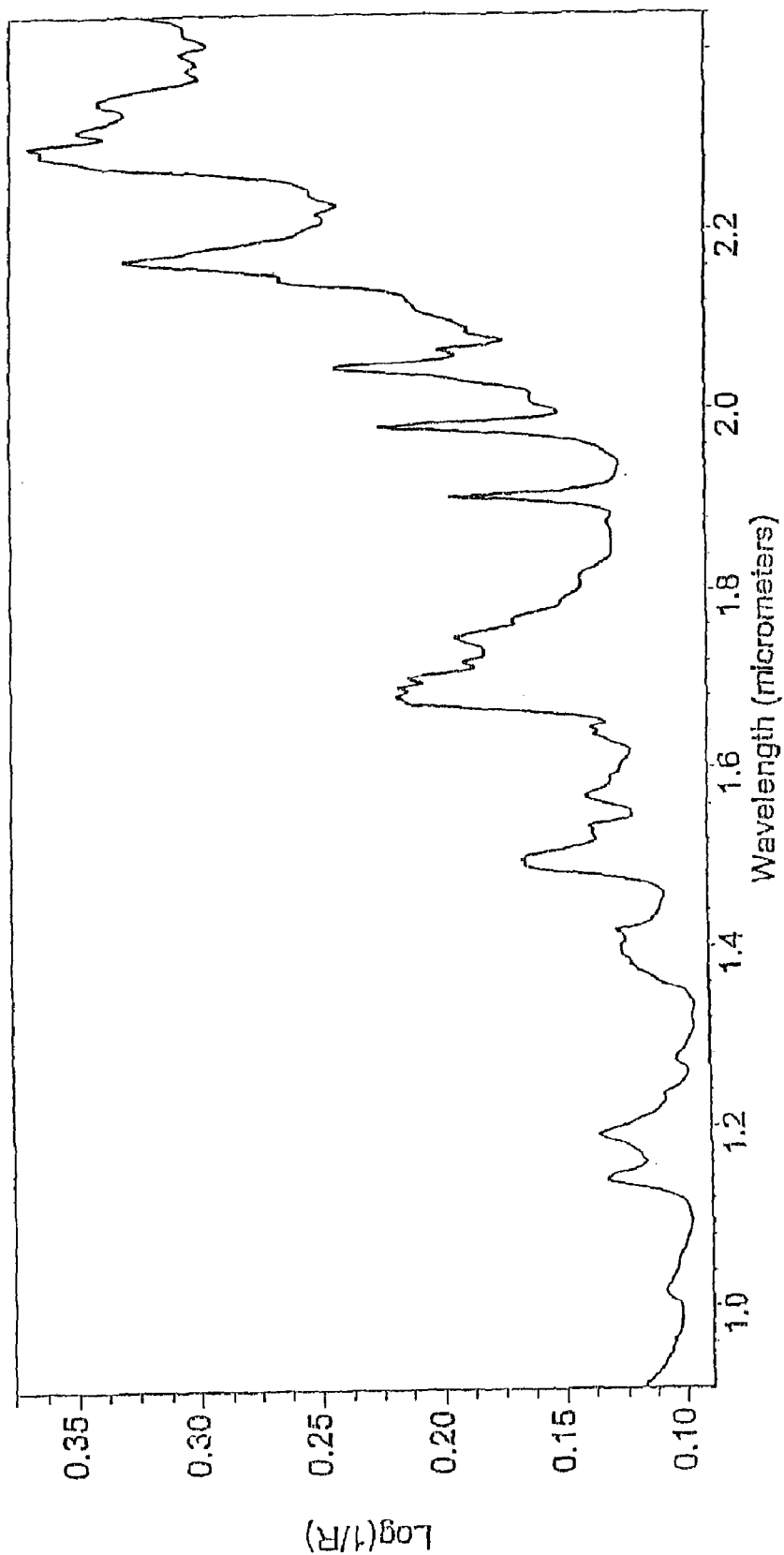
FIG. 27 is the solid state FT near infrared spectrum of the Type IV non-solvated crystal form of lopinavir.
Figure 29:
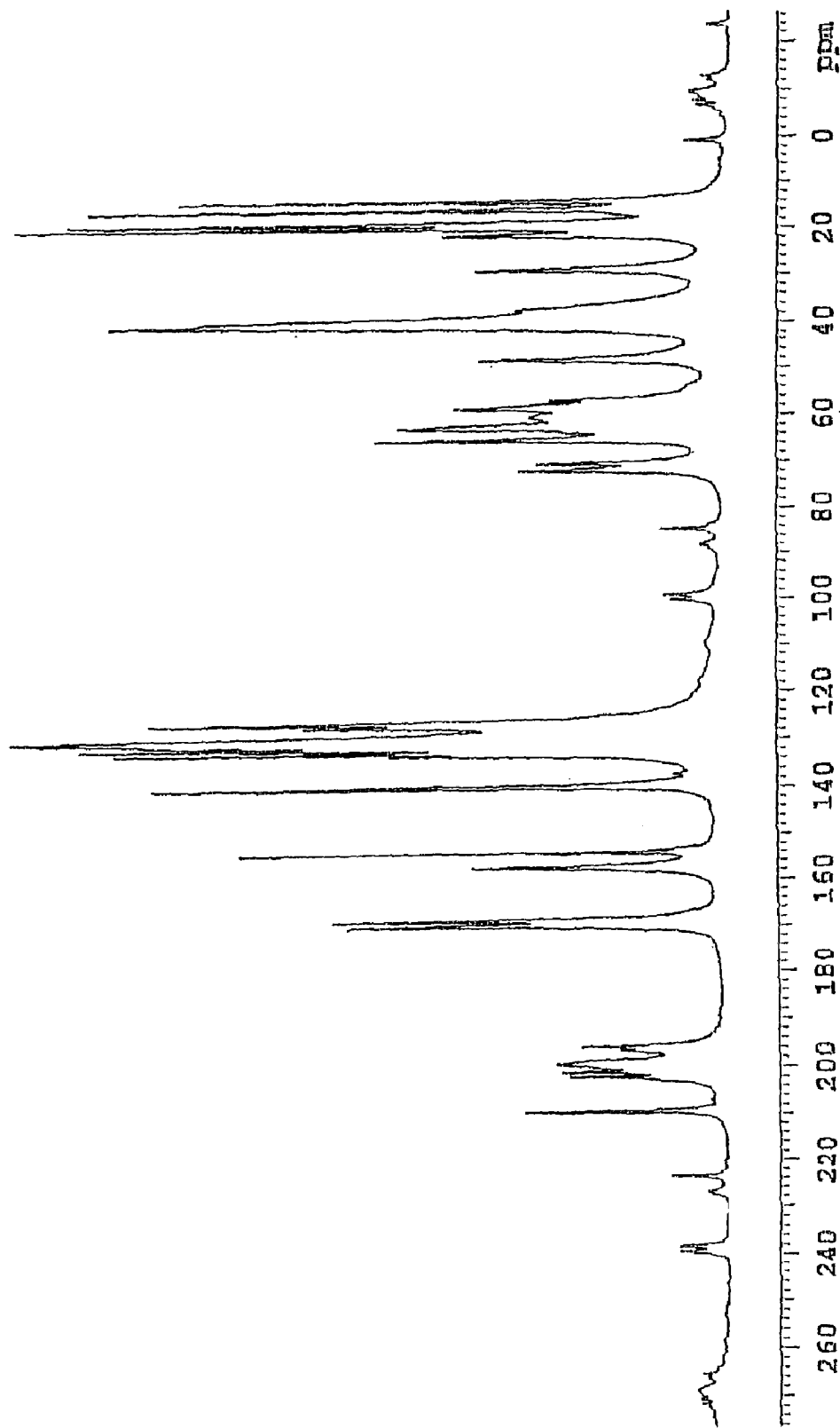
FIG. 29 is the 100 MHz solid state $^{13}$C nuclear magnetic resonance spectrum of the Type IV non-solvated crystal form of lopinavir.
Figure 30:
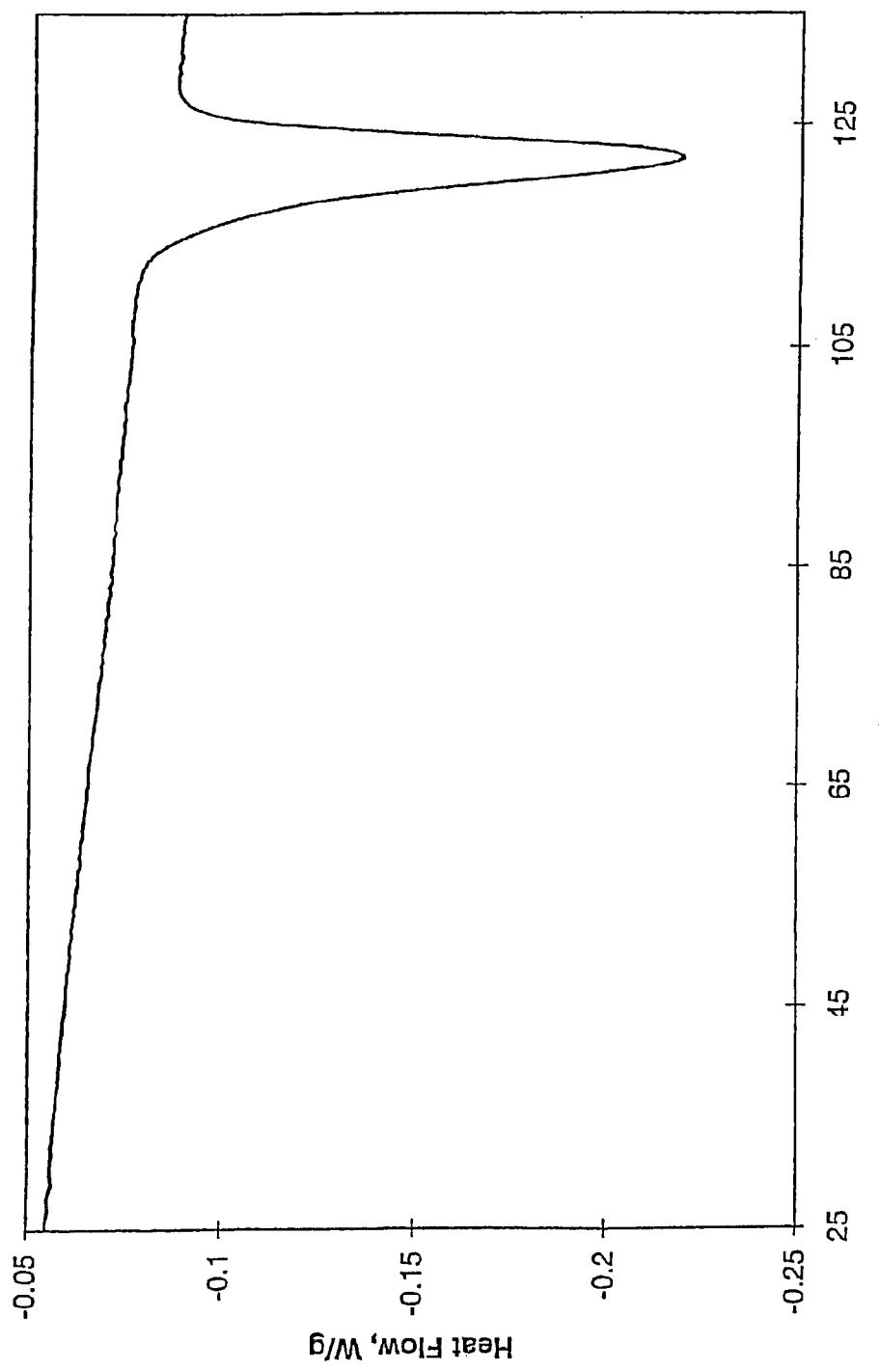
FIG. 30 is the differential scanning calorimetric (DSC) thermogram for the Type IV non-solvated crystal form of lopinavir.

Lopinavir (259 g) was dissolved in 500 g of acetonitrile at 40-42° C. The hazy solution was filtered through a 0.45 ③ Nylon membrane into a 2 L round bottom flask and the solution was seeded with a few crystals of the product of Example 16. The flask was rotated at 10-20 rpm overnight without heat or vacuum using a rotary evaporator apparatus. A thick slurry of needle-like crystals resulted. The slurry was cooled in an ice bath for 1 hour and then filtered in a table-top Neutsche filter blanketed with nitrogen and covered with plastic film. The filter cake was washed with acetonitrile and sucked dry under nitrogen for about 30 minutes. The filter cake was transferred to a crystallizing dish and dried over a weekend at 60-65° C. at 20-21" Hg with a nitrogen bleed to provide 194.3 g of the Type IV non-solvated crystal form of lopinavir. The product was crystalline by powder X-ray diffractometry and was classified as the Type IV non-solvated crystal form of lopinavir by solid state FT mid-IR. Solid state FT mid-IR (FIG. 26). Solid state FT near IR (FIG. 27). Powder X-ray diffraction pattern (FIG. 28). 100 MHz solid state $^{13}C$ nuclear magnetic resonance spectrum (FIG. 29). DSC thermogram (FIG. 30). The product contained less than 0.1% volatile material by thermal gravimetric analysis.

When administered for treatment of an HIV infection, lopinavir is preferably administered in combination with ritonavir in a ratio of 4:1 (lopinavir:ritonavir). A preferred pharmaceutical composition for administering lopinavir, comprising a 4:1 ratio of lopinavir:ritonavir has the following composition, encapsulated in a soft elastic gelatin capsule.

| Lopinavir | 133.3 mg |
| Ritonavir | 33.3 mg |
| Oleic acid, NF | 598.6 mg |
| Propylene Glycol, USP | 64.1 mg |
| Polyoxyl 35 Castor Oil, NF (Cremephor EL ®) | 21.4 mg |
| Water, purified, USP (distilled) | 4.3 mg |

If a hydrated or solvated crystal form of lopinavir is used in the composition, the amount of the hydrated or solvated crystal form of lopinavir is adjusted to take into account the amount of water or other solvent present in the crystal form.

The preferred composition can be prepared according to the following method.

The following protocol is employed in the preparation of 1000 soft gelatin capsules:

| Scale (mg/capsule) | Name | Amount (g) |
|---|---|---|
| Q.S. | Nitrogen, N.F. | Q.S. |
| 578.6 | Oleic Acid, NF | 578.6 |
| 33.3 | Ritonavir | 33.3 |
| 64.1 | Propylene Glycol, USP | 64.1 |
| 4.3 | Water, purified, USP (distilled) | 4.3 |
| 133.3 | Lopinavir | 133.3 |
| 10.0 | Oleic Acid, NF | 10.0 |
| 21.4 | Polyoxyl 35 Castor Oil, NF | 21.4 |
| 10.0 | Oleic Acid, NF | 10.0 |

A mixing tank and suitable container are purged with nitrogen. 578.6 g of oleic acid is then charged into the mixing tank. The mixing tank is heated to 28° C. (not to exceed 31° C.) and mixing is started. 33.3 g of ritonavir is then added to the oleic acid with mixing. The propylene glycol and water are added to the mixing tank and mixing is continued until the solution is clear. 133.3 g of lopinavir is then added into the mixing tank and mixing is continued. 10 g of oleic acid is then charged into the tank and mixed until the solution is clear. 21.4 g of polyoxyl 35 castor oil, NF is added to the mixing tank and mixing is continued, followed by the addition of 10 g of oleic acid.

The solution is stored at 2-8° C. until encapsulation. 0.855 g of the solution is filled into each soft gelatin capsule and the soft gelatin capsules are then dried, and stored at 2-8° C.

As used herein, the term "substantially pure", when used in reference to a crystalline form of lopinavir, refers to that crystalline form of lopinavir which is greater than about 90% pure. This means that the crystalline form of lopinavir does not contain more than about 10% of any other compound and, in particular, does not contain more than about 10% of any other form of lopinavir, such as amorphous, solvated forms, non-solvated forms and desolvated forms. More preferably, the term "substantially pure" refers to a crystalline form of lopinavir which is greater than about 95% pure. This means that the crystalline form of lopinavir does not contain more than about 5% of any other compound and, in particular, does not contain more than about 5% of any other form of lopinavir, such as amorphous, solvated forms, non-solvated forms and desolvated forms. Even more preferably, the term "substantially pure" refers to a crystalline form of lopinavir which is greater than about 97% pure. This means that the crystalline form of lopinavir does not contain more than about 3% of any other compound and, in particular, does not contain more than about 3% of any other form of lopinavir, such as amorphous, solvated forms, non-solvated forms and desolvated forms.

Yet even more preferably, the term "substantially pure" refers to a crystalline form of lopinavir which is greater than about 98% pure. This means that the crystalline form of lopinavir does not contain more than about 2% of any other compound and, in particular, does not contain more than about 2% of any other form of lopinavir, such as amorphous, solvated forms, non-solvated forms and desolvated forms.

Most preferably, the term "substantially pure" refers to a crystalline form of lopinavir which is greater than about 99% pure. This means that the crystalline form of lopinavir does not contain more than about 1% of any other compound and, in particular, does not contain more than about 1% of any other form of lopinavir, such as amorphous, solvated forms, non-solvated forms and desolvated forms.

Powder X-ray diffraction analysis of samples was conducted in the following manner. Samples for X-ray diffraction analysis were prepared by spreading the sample powder (ground to a fine powder with a mortar and pestle, or with glass microscope slides for limited quantity samples) in a thin layer on the sample holder and gently flattening the sample with a microscope slide. Samples were run in one of three configurations: circular bulk holder, a quartz zero background plate or hot stage mount (similar mounting to a zero background plate). X-ray powder diffraction was performed using an XDS 2000 θ/θ diffractometer (Scintag; 2 kW normal focus X-ray tube with either a liquid nitrogen or Peltier cooled germanium solid state detector; 45 kV and 30-40 ma; X-ray source: Cu-Kα1; Range: 2.00-40.00° Two Theta; Scan Rate: 0.5 or 2 degrees/minute), a XRD-6000 diffractometer (Shimadzu; fine focus X-ray tube with a NaI scintillation detector; 40-45 kV and 30-40 ma; X-ray source: Cu-Kα1; Range: 2.00-40.00° Two Theta; Scan Rate: 2 degrees/minute) or a I-2 X-ray diffractometer (Nicolet; scintillation detector; 50 kV and 30 ma; X-ray source: Cu-Kα1; Range: 2.00-40.00° Two Theta; Scan Rate: 2 degrees/minute. The relative humidity of the sample in the hot stage mount could be controlled using a relative humidity generator (model RH200, VTI Corp.).

Characteristic powder X-ray diffraction pattern peak positions are reported for polymorphs in terms of the angular positions (two theta) with an allowable variability of ±0.1°. This allowable variability is specified by the U.S. Pharmacopeia, pages 1843-1844 (1995). The variability of ±0.1° is intended to be used when comparing two powder X-ray diffraction patterns. In practice, if a diffraction pattern peak from one pattern is assigned a range of angular positions (two theta) which is the measured peak position ±0.1° and a diffraction pattern peak from the other pattern is assigned a range of angular positions (two theta) which is the measured peak position ±0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.10°-5.30°. If a comparison peak from the other diffraction pattern is determined to have a peak position of 5.35°, for comparison purposes the allowable variability allows the peak to be assigned a position in the range of 5.25°-5.45°. Because there is overlap between the two ranges of peak positions (i.e., 5.10°-5.30° and 5.25°-5.45°) the two peaks being compared are considered to have the same angular position (two theta).

Solid state nuclear magnetic resonance analysis of samples was conducted in the following manner. A Bruker AMX-400 instrument was used with the following parameters: CP-MAS (cross-polarized magic angle spinning); spectrometer frequency for $^{13}C$ was 100.6 MHz; pulse sequence was VA-CP2LEV; contact time was 2.5 milliseconds; spin rate was 7000 Hz; recycle delay time was 5.0 sec; 3000 scans).

FT near infrared analysis of samples was conducted in the following manner. Samples were analyzed as neat, undiluted powders contained in a clear glass 1 dram vial. A Nicolet Magna System 750 FT-IR spectrometer with a Nicolet SabIR near infrared diffuse reflectance fiber optic probe accessory was used with the following parameters: the detector was PbS; the beamsplitter was CaF2; the number of sample scans was 16; the resolution was 8 cm-1.

FT mid infrared analysis of samples was conducted in the following manner. Samples were analyzed as neat, undiluted powders. A Nicolet Magna System 750 FT-IR spectrometer with a Nicolet NIC-PLAN Microscope with a MCT-A liquid nitrogen cooled detector was used. The sample was placed on a 13 mm×1 mm BaF2 disc sample holder. 64 scans were collected at 4 cm-1 resolution.

Differential scanning calorimetric analysis of samples was conducted in the following manner. A T.A. Instruments Model 2920 differential scanning calorimeter with TA Instruments DSC cell with Thermal Solutions version 2.3 software for data analysis. The analysis parameters were: Sample size: 4-10 mg, placed in an aluminum pan and sealed after a pin hole was poked in the lid; Heating rate: 1° C./minute under a dry nitrogen purge (40-50 mL/minute).

Thermal gravimetric analysis was conducted by heating the sample at 1° C. or 5° C./minute from ambient to 200° C.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for preparing a pharmaceutical composition comprising (2S,3 S,5S)-2-(2,6-dimethylphenoxyacetyl)-amino-3-hydroxy-5-(2-(1-tetrahydropyrimid-2-onyl)-3-methylbutanoyl)amino-1,6-diphenylhexane (lopinavir), said process comprising:

combining a crystalline form of lopinavir and additional ingredients, wherein said crystalline form of lopinavir is selected from the group consisting of:

a hydrated crystalline form of lopinavir with a peak in the solid state infrared spectrum at a position within the range 1652-1666 $cm^{-1}$ and a peak in the solid state infrared spectrum at a position within the range 1606-1615 $cm^{-1}$, wherein said peaks have at least a moderately strong intensity;

a solvated crystalline form of lopinavir with a peak in the solid state infrared spectrum at a position within the range 1661-1673 $cm^{-1}$, a peak in the solid state infrared spectrum at a position within the range 1645-1653 $cm^{-1}$ and a peak in the solid state infrared spectrum at a position within the range 1619-1629 $cm^{-1}$, wherein said peaks have at least a moderately strong intensity;

a crystalline form of lopinavir with a peak in the solid state infrared spectrum at a position within the range 1655-1662 $cm^{-1}$, wherein said peak has at least a moderately strong intensity;

a crystalline form of lopinavir with a peak in the solid state infrared spectrum at a position within the range 1655-1662 $cm^{-1}$ and a peak in the solid state infrared spectrum at a position within the range 1636-1647 $cm^{-1}$, wherein said peaks have at least a moderately strong intensity;

a solvated crystalline form of lopinavir with a peak in the solid state infrared spectrum at a position within the range 1655-1662 $cm^{-1}$, wherein said peak has at least a moderately strong intensity;

a solvated crystalline form of lopinavir with a peak in the solid state infrared spectrum at a position within the range 1655-1662 $cm^{-1}$ and a peak in the solid state infrared spectrum at a position within the range 1636-1647 $cm^{-1}$, wherein said peaks have at least a moderately strong intensity;

a non-solvated crystalline form of lopinavir with a peak in the solid state infrared spectrum at a position within the range 1680-1685 $cm^{-1}$ and a peak in the solid state infrared spectrum at a position within the range 1625-1630 $cm^{-1}$, wherein said peaks have at least a moderately strong intensity;

a non-solvated crystalline form of lopinavir with characteristic peaks in the powder X-ray diffraction pattern at values of two theta of 6.85°±0.1°, 9.14°±0.1°, 12.88°±0.1°, 15.09°±0.1°, 17.74°±0.1°, 18.01°±0.1° and 18.53°±0.1°;

a non-solvated crystalline form of lopinavir with characteristic peaks in the powder X-ray diffraction pattern at values of two theta of 6.85°±0.1°, 9.14°±0.1°, 10.80°±0.1°, 12.04°±0.1°, 12.88°±0.1°, 15.09°±0.1°, 17.74°±0.1°, 18.01°±0.1°, 18.26°±0.1°, 18.53°±0.1°, 20.47°±0.1° and 25.35°±0.1°;

a non-solvated crystalline form of lopinavir with a peak in the solid state infrared spectrum at a position within the range 1680-1685 $cm^{-1}$ and a peak in the solid state infrared spectrum at a position within the range 1668-1674 $cm^{-1}$ and a peak in the solid state infrared spectrum at a position within the range 1656-1662 $cm^{-1}$ and a peak in the solid state infrared spectrum at a position within the range 1642-1648 $cm^{-1}$ and a peak in the solid state infrared spectrum at a position within the range 1625-1630 $cm^{-1}$, wherein said peaks have at least a moderately strong intensity;

a desolvated crystalline form of lopinavir with a peak in the solid state infrared spectrum at a position within the range 1655-1662 $cm^{-1}$, wherein said peak has at least a moderately strong intensity;

a desolvated crystalline form of lopinavir with a peak in the solid state infrared spectrum at a position within the range 1655-1662 $cm^{-1}$ and a peak in the solid state infrared spectrum at a position within the range 1636-1647 $cm^{-1}$, wherein said peaks have at least a moderately strong intensity;

a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°; and a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

2. The process according to claim 1, wherein said additional ingredients comprise ritonavir.

3. A process for preparing a pharmaceutical composition comprising lopinavir, said process comprising:

combining lopinavir that comprises a crystalline form of lopinavir with additional ingredients, wherein said crystalline form of lopinavir is selected from the group consisting of:

a hydrated crystalline form of lopinavir with a peak in the solid state infrared spectrum at a position within the range 1652-1666 $cm^{-1}$ and a peak in the solid state infrared spectrum at a position within the range 1606-1615 $cm^{-1}$, wherein said peaks have at least a moderately strong intensity;

a solvated crystalline form of lopinavir with a peak in the solid state infrared spectrum at a position within the range 1661-1673 $cm^{-1}$, a peak in the solid state infrared spectrum at a position within the range 1645-1653 $cm^{-1}$ and a peak in the solid state infrared spectrum at a position within the range 1619-1629 $cm^{-1}$, wherein said peaks have at least a moderately strong intensity;

a crystalline form of lopinavir with a peak in the solid state infrared spectrum at a position within the range 1655-1662 $cm^{-1}$;

a crystalline form of lopinavir with a peak in the solid state infrared spectrum at a position within the range 1655-1662 $cm^{-1}$ and a peak in the solid state infrared spectrum at a position within the range 1636-1647 $cm^{-1}$, wherein said peaks have at least a moderately strong intensity;

a solvated crystalline form of lopinavir with a peak in the solid state infrared spectrum at a position within the range 1655-1662 $cm^{-1}$, wherein said peak has at least a moderately strong intensity;

a solvated crystalline form of lopinavir with a peak in the solid state infrared spectrum at a position within the range 1655-1662 $cm^{-1}$ and a peak in the solid state infrared spectrum at a position within the range 1636-1647 $cm^{-1}$, wherein said peaks have at least a moderately strong intensity;

a non-solvated crystalline form of lopinavir with a peak in the solid state infrared spectrum at a position within the range 1680-1685 $cm^{-1}$ and a peak in the solid state infrared spectrum at a position within the range 1625-1630 $cm^{-1}$, wherein said peaks have at least a moderately strong intensity;

a non-solvated crystalline form of lopinavir with characteristic peaks in the powder X-ray diffraction pattern at values of two theta of 6.85°±0.1°, 9.14°±0.1°, 12.88°±0.1°, 15.09°±0.1°, 17.74°±0.1°, 18.01°±0.1° and 18.53°±0.1°;

a non-solvated crystalline form of lopinavir with characteristic peaks in the powder X-ray diffraction pattern at values of two theta of 6.85°±0.1°, 9.14°±0.1°, 10.80°±0.1°, 12.04°±0.1°, 12.88°±0.1°, 15.09°±0.1°, 17.74°±0.1°, 18.01°±0.1°, 18.26°±0.1°, 18.53°±0.1°, 20.47°±0.1° and 25.35°±0.1°;

a non-solvated crystalline form of lopinavir with a peak in the solid state infrared spectrum at a position within the range 1680-1685 cm$^{-1}$ and a peak in the solid state infrared spectrum at a position within the range 1668-1674 cm$^{-1}$ and a peak in the solid state infrared spectrum at a position within the range 1656-1662 cm$^{-1}$ and a peak in the solid state infrared spectrum at a position within the range 1642-1648 cm$^{-1}$ and a peak in the solid state infrared spectrum at a position within the range 1625-1630 cm$^{-1}$, wherein said peaks have at least a moderately strong intensity;

a desolvated crystalline form of lopinavir with a peak in the solid state infrared spectrum at a position within the range 1655-1662 cm$^{-1}$, wherein said peak has at least a moderately strong intensity;

a desolvated crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity;

a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°; and a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

4. A process for preparing a pharmaceutical composition comprising lopinavir, said process comprising:
combining a hydrated crystalline form of lopinavir and additional ingredients,
wherein said hydrated crystalline form of lopinavir is selected from the group consisting of:
a hydrated crystalline form of lopinavir with a peak in the solid state infrared spectrum at a position within the range 1652-1666 cm$^{-1}$ and a peak in the solid state infrared spectrum at a position within the range 1606-1615 cm$^{-1}$, wherein said peaks have at least a moderately strong intensity;
a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°; and
a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

5. The process of claim 4, wherein said hydrated crystalline form of lopinavir comprises about 0.5 molecules of water per molecule of lopinavir.

6. The process of claim 4, wherein said hydrated crystalline form of lopinavir comprises from about 0.5 molecules of water per molecule of lopinavir to about 2 molecules of water per molecule of lopinavir.

7. The process according to claim 1, wherein said crystalline form of lopinavir is a hydrated crystalline form of lopinavir with a peak in the solid state infrared spectrum at a position within the range 1652-1666 cm$^{-1}$ and a peak in the solid state infrared spectrum at a position within the range 1606-1615 cm$^{-1}$, wherein said peaks have at least a moderately strong intensity.

8. The process according to claim 1, wherein said crystalline form of lopinavir is a solvated crystalline form of lopinavir with a peak in the solid state infrared spectrum at a position within the range 1661-1673 cm$^{-1}$, a peak in the solid state infrared spectrum at a position within the range 1645-1653 cm$^{-1}$ and a peak in the solid state infrared spectrum at a position within the range 1619-1629 cm$^{-1}$, wherein said peaks have at least a moderately strong intensity.

9. The process according to claim 1, wherein said crystalline form of lopinavir is a crystalline form of lopinavir with a peak in the solid state infrared spectrum at a position within the range 1655-1662 cm$^{-1}$, wherein said peak has at least a moderately strong intensity.

10. The process according to claim 1, wherein said crystalline form of lopinavir is a crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity.

11. The process according to claim 1, wherein said crystalline form of lopinavir is a solvated crystalline form of lopinavir with a peak in the solid state infrared spectrum at a position within the range 1655-1662 cm$^{-1}$, wherein said peak has at least a moderately strong intensity.

12. The process according to claim 1, wherein said crystalline form of lopinavir is a solvated crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity.

13. The process according to claim 1, wherein said crystalline form of lopinavir is a non-solvated crystalline form of lopinavir with a peak in the solid state infrared spectrum at a position within the range 1680-1685 cm$^{-1}$ and a peak in the solid state infrared spectrum at a position within the range 1625-1630 cm$^{-1}$, wherein said peaks have at least a moderately strong intensity.

14. The process according to claim 1, wherein said crystalline form of lopinavir is a non-solvated crystalline form of lopinavir with characteristic peaks in the powder X-ray diffraction pattern at values of two theta of 6.85°±0.1°, 9.14°±0.1°, 12.88°±0.1°, 15.09°±0.1°, 17.74°±0.1°, 18.01°±0.1° and 18.53°±0.1°.

15. The process according to claim 1, wherein said crystalline form of lopinavir is a non-solvated crystalline form of lopinavir with characteristic peaks in the powder X-ray diffraction pattern at values of two theta of 6.85°±0.1°, 9.14°±0.1°, 10.80°±0.1°, 12.04°±0.1°, 12.88°±0.1°, 15.09°±0.1°, 17.74°±0.1°, 18.01°±0.1°, 18.26°±0.1°, 18.53°±0.1°, 20.47°±0.1° and 25.35°±0.1°.

16. The process according to claim 1, wherein said crystalline form of lopinavir is a non-solvated crystalline form of lopinavir with a peak in the solid state infrared spectrum at a position within the range 1680-1685 cm$^{-1}$ and a peak in the solid state infrared spectrum at a position within the range 1668-1674 cm$^{-1}$ and a peak in the solid state infrared spectrum at a position within the range 1656-1662 cm$^{-1}$ and a peak in the solid state infrared spectrum at a position within the range 1642-1648 cm$^{-1}$ and a peak in the solid state infrared spectrum at a position within the range 1625-1630 cm$^{-1}$, wherein said peaks have at least a moderately strong intensity.

17. The process according to claim 1, wherein said crystalline form of lopinavir is a desolvated crystalline form of lopinavir with a peak in the solid state infrared spectrum at a position within the range 1655-1662 cm$^{-1}$, wherein said peak has at least a moderately strong intensity.

18. The process according to claim 1, wherein said crystalline form of lopinavir is a desolvated crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity.

19. The process according to claim 1, wherein said crystalline form of lopinavir is a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°.

20. The process according to claim 1, wherein said crystalline form of lopinavir is a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

21. The process according to claim 3, wherein said crystalline form of lopinavir is a hydrated crystalline form of lopinavir with a peak in the solid state infrared spectrum at a position within the range 1652-1666 cm$^{-1}$ and a peak in the solid state infrared spectrum at a position within the range 1606-1615 cm$^{-1}$, wherein said peaks have at least a moderately strong intensity.

22. The process according to claim 3, wherein said crystalline form of lopinavir is a solvated crystalline form of lopinavir with a peak in the solid state infrared spectrum at a position within the range 1661-1673 cm$^{-1}$, a peak in the solid state infrared spectrum at a position within the range 1645-1653 cm$^{-1}$ and a peak in the solid state infrared spectrum at a position within the range 1619-1629 cm$^{-1}$, wherein said peaks have at least a moderately strong intensity.

23. The process according to claim 3, wherein said crystalline form of lopinavir is a crystalline form of lopinavir with a peak in the solid state infrared spectrum at a position within the range 1655-1662 cm$^{-1}$, wherein said peak has at least a moderately strong intensity.

24. The process according to claim 3, wherein said crystalline form of lopinavir is a crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity.

25. The process according to claim 3, wherein said crystalline form of lopinavir is a solvated crystalline form of lopinavir with a peak in the solid state infrared spectrum at a position within the range 1655-1662 cm$^{-1}$, wherein said peak has at least a moderately strong intensity.

26. The process according to claim 3, wherein said crystalline form of lopinavir is a solvated crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity.

27. The process according to claim 3, wherein said crystalline form of lopinavir is a non-solvated crystalline form of lopinavir with a peak in the solid state infrared spectrum at a position within the range 1680-1685 cm$^{-1}$ and a peak in the solid state infrared spectrum at a position within the range 1625-1630 cm$^{-1}$, wherein said peaks have at least a moderately strong intensity.

28. The process according to claim 3, wherein said crystalline form of lopinavir is a non-solvated crystalline form of lopinavir with characteristic peaks in the powder X-ray diffraction pattern at values of two theta of 6.85°±0.1°, 9.14°±0.1°, 12.88°±0.1°, 15.09°±0.1°, 17.74°±0.1°, 18.01°±0.1° and 18.53°±0.1°.

29. The process according to claim 3, wherein said crystalline form of lopinavir is a non-solvated crystalline form of lopinavir with characteristic peaks in the powder X-ray diffraction pattern at values of two theta of 6.85°±0.1°, 9.14°±0.1°, 10.80°±0.1°, 12.04°±0.1°, 12.88°±0.1°, 15.09°±0.1°, 17.74°±0.1°, 18.01°±0.1°, 18.26°±0.1°, 18.53°±0.1°, 20.47°±0.1° and 25.35°±0.1°.

30. The process according to claim 3, wherein said crystalline form of lopinavir is a non-solvated crystalline form of lopinavir with a peak in the solid state infrared spectrum at a position within the range 1680-1685 cm$^{-1}$ and a peak in the solid state infrared spectrum at a position within the range 1668-1674 cm$^{-1}$ and a peak in the solid state infrared spectrum at a position within the range 1656-1662 cm$^{-1}$ and a peak in the solid state infrared spectrum at a position within the range 1642-1648 cm$^{-1}$ and a peak in the solid state infrared spectrum at a position within the range 1625-1630 cm$^{-1}$, wherein said peaks have at least a moderately strong intensity.

31. The process according to claim 3, wherein said crystalline form of lopinavir is a desolvated crystalline form of lopinavir with a peak in the solid state infrared spectrum at a position within the range 1655-1662 cm$^{-1}$, wherein said peak has at least a moderately strong intensity.

32. The process according to claim 3, wherein said crystalline form of lopinavir is a desolvated crystalline form of lopinavir with a peak in the solid state infrared spectrum at a position within the range 1655-1662 cm$^{-1}$ and a peak in the solid state infrared spectrum at a position within the range 1636-1647 cm$^{-1}$, wherein said peaks have at least a moderately strong intensity.

33. The process according to claim 3, wherein said crystalline form of lopinavir is a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°.

34. The process according to claim 3, wherein said crystalline form of lopinavir is a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

35. The process according to claim 3, wherein said additional ingredients comprise ritonavir.

36. The process according to claim 4, wherein said hydrated crystalline form of lopinavir is a hydrated crystalline form of lopinavir with a peak in the solid state infrared spectrum at a position within the range 1652-1666 cm$^{-1}$ and a peak in the solid state infrared spectrum at a position within the range 1606-1615 cm$^{-1}$, wherein said peaks have at least a moderately strong intensity.

37. The process according to claim 4, wherein said hydrated crystalline form of lopinavir is a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.57°±0.1°, 18.30°±0.1°, 18.95°±0.1° and 22.74°±0.1°.

38. The process according to claim 4, wherein said hydrated crystalline form of lopinavir is a higher hydrated crystalline form of lopinavir with characteristic peaks in the powder X-ray diffraction pattern at values of two theta of 3.89°±0.1°, 6.55°±0.1°, 7.76°±0.1°, 8.55°±0.1°, 9.70°±0.1°, 10.56°±0.1°, 14.76°±0.1°, 15.06°±0.1°, 15.57°±0.1°, 16.49°±0.1°, 17.51°±0.1°, 18.30°±0.1°, 18.95°±0.1°, 21.73°±0.1° and 22.74°±0.1°.

39. The process according to claim 4, wherein said additional ingredients comprise ritonavir.

* * * * *